US011986597B2

(12) United States Patent
Martin et al.

(10) Patent No.: US 11,986,597 B2
(45) Date of Patent: May 21, 2024

(54) NITRIC OXIDE GENERATING SYSTEMS FOR INHALATION

(71) Applicant: NOTA Laboratories, LLC, Ann Arbor, MI (US)

(72) Inventors: Glenn Martin, Redford Township, MI (US); Andrew P. Hunt, Ann Arbor, MI (US); Maria Kim, Ann Arbor, MI (US); Mark E. Meyerhoff, Ann Arbor, MI (US); Malcolm Kahn, Franklin Lakes, NJ (US)

(73) Assignee: NOTA Laboratories, LLC, Ann Arbor, MI (US)

( * ) Notice: Subject to any disclaimer, the term of this patent is extended or adjusted under 35 U.S.C. 154(b) by 242 days.

(21) Appl. No.: 17/182,868

(22) Filed: Feb. 23, 2021

(65) Prior Publication Data

US 2021/0178106 A1    Jun. 17, 2021

Related U.S. Application Data

(63) Continuation-in-part of application No. 16/846,063, filed on Apr. 10, 2020.

(Continued)

(51) Int. Cl.
*A61M 16/14*     (2006.01)
*A61K 9/00*      (2006.01)
(Continued)

(52) U.S. Cl.
CPC ........... *A61M 16/14* (2013.01); *A61K 9/0073* (2013.01); *A61K 31/16* (2013.01); *A61K 33/00* (2013.01);
(Continued)

(58) Field of Classification Search
CPC .............. A61K 31/095; A61K 31/7036; A61K 9/0043; A61K 9/145; A61K 45/06;
(Continued)

(56) References Cited

U.S. PATENT DOCUMENTS 6,403,597 B1 *  6/2002  Wilson ................... A61K 45/06
                                                   514/256
6,805,124 B2   10/2004  Japuntich et al.
(Continued)

FOREIGN PATENT DOCUMENTS

WO   WO-2019169092 A1 *  9/2019  ............. A61K 31/04

OTHER PUBLICATIONS

James N. Smith, Tara P. Dasgupta, "Kinetics and Mechanism of the Decomposition of S-Nitrosoglutathione by -Ascorbic Acid and Copper Ions in Aqueous Solution to Produce Nitric Oxide", vol. 4, Issue 1, Feb. 2000, pp. 57-66. (Year: 2000).*

*Primary Examiner* — Bradley H Philips
*Assistant Examiner* — Savannah L Gabriel
(74) *Attorney, Agent, or Firm* — Dierker & Kavanaugh, P.C.

(57) ABSTRACT

A moisture or hydrating liquid activatable solid formulation for nitric oxide (NO) generation includes a nitrite source; a copper (I) or copper (II) catalyst; an NO generation accelerant; and a solid pH buffer. The nitrite source is to generate NO when exposed to an effective amount of moisture or a hydrating liquid. The pH buffer is present in an amount sufficient to render a pH of the moisture or hydrating liquid activatable solid formulation from greater than 4 to about 9.0.

18 Claims, 25 Drawing Sheets

Related U.S. Application Data

(60) Provisional application No. 62/891,129, filed on Aug. 23, 2019.

(51) Int. Cl.
| | |
|---|---|
| *A61K 31/16* | (2006.01) |
| *A61K 33/00* | (2006.01) |
| *A61K 47/02* | (2006.01) |
| *A61K 47/18* | (2017.01) |
| *A61K 47/20* | (2006.01) |
| *A61K 47/22* | (2006.01) |
| *A61K 47/24* | (2006.01) |
| *A61M 16/06* | (2006.01) |
| *C01B 21/24* | (2006.01) |

(52) U.S. Cl.
CPC ............ *A61K 47/02* (2013.01); *A61K 47/183* (2013.01); *A61K 47/20* (2013.01); *A61K 47/22* (2013.01); *A61K 47/24* (2013.01); *A61M 16/06* (2013.01); *C01B 21/24* (2013.01); A61M 2202/0275 (2013.01); A61M 2202/062 (2013.01)

(58) Field of Classification Search
CPC ...... A61K 9/0073; A61K 31/16; A61K 33/00; A61K 47/20; A61K 47/22; A61K 47/24; A61M 16/14; A61M 16/06; A61M 2202/0275; A61M 2202/062; C01B 21/24
See application file for complete search history.

(56) References Cited

U.S. PATENT DOCUMENTS

| | | | |
|---|---|---|---|
| 7,044,127 | B1 | 5/2006 | Fernandez DeCastro |
| 7,958,889 | B1 | 6/2011 | Fernandez-Decastro |
| 8,399,005 | B2 | 3/2013 | Schoenfisch et al. |
| 9,278,111 | B2 | 3/2016 | Montgomery et al. |
| 9,445,996 | B2 * | 9/2016 | Chen ................. A61K 31/19 |
| 11,472,705 | B2 * | 10/2022 | Regev ................ A01N 59/00 |
| 2001/0037810 | A1 | 11/2001 | Fine et al. |
| 2003/0062043 | A1 * | 4/2003 | Fine .................. A61K 33/00 128/203.12 |
| 2005/0142217 | A1 * | 6/2005 | Adams ............... A61K 33/00 424/718 |
| 2009/0112193 | A1 | 4/2009 | Hyde et al. |
| 2009/0118819 | A1 * | 5/2009 | Merz ................. A61L 31/10 623/1.42 |
| 2010/0108071 | A1 | 5/2010 | Macy, Jr. |
| 2012/0093948 | A1 * | 4/2012 | Fine .................. A61P 25/34 424/718 |
| 2014/0079762 | A1 * | 3/2014 | Perricone ............ A61K 47/24 424/450 |
| 2014/0369949 | A1 * | 12/2014 | Peters ................. A61K 8/84 424/78.02 |
| 2016/0166525 | A1 * | 6/2016 | Ischiropoulos ........ A61P 3/00 514/562 |
| 2017/0209663 | A1 * | 7/2017 | Miller ............... A61M 16/125 |
| 2018/0207323 | A1 | 7/2018 | Chen et al. |
| 2019/0054038 | A1 * | 2/2019 | Meyerhoff ............ A61K 9/08 |
| 2019/0367366 | A1 * | 12/2019 | Regev ................ A61K 47/02 |
| 2020/0361772 | A1 * | 11/2020 | Hall ................ B01D 53/0415 |

* cited by examiner

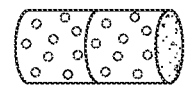
FIG. 1A
FIG. 1B
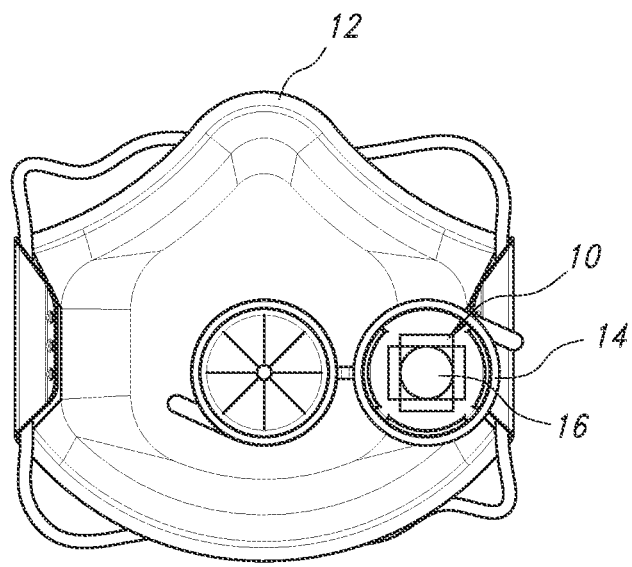
FIG. 2A

NITRIC OXIDE GENERATING SYSTEMS FOR INHALATION

CROSS-REFERENCE TO RELATED APPLICATIONS

This application is a continuation-in-part of U.S. application Ser. No. 16/846,063, filed Apr. 10, 2020, which itself claims the benefit of U.S. provisional application Ser. No. 62/891,129, filed Aug. 23, 2019, the contents of each of which is incorporated by reference herein in its entirety.

BACKGROUND

In the human body, nitric oxide (NO) may be produced by any of several isoforms of the enzyme nitric oxide synthase (NOS). NO is central to the mammalian immune response or defense, and is a cytotoxic agent in the mechanisms used by macrophages to kill *L. major, M. bovis*, and *M. tuberculosis*, among numerous other species of bacteria. NO is also an effective antiviral agent, that has activity against the rhinovirus that causes common colds. NO is produced from L-arginine in the airways (e.g., in the upper respiratory tract) by immune cells (macrophages, neutrophils, lymphocytes, etc.) and airway epithelial cells (e.g., conductive and respiratory epithelial cells) primarily through inducible nitric oxide synthase (iNOS). Deficiencies in NO production can lead to decreased immune response and/or microbial biofilm formation. The deficiencies in nasal NO levels have been linked with diseases, such as primary ciliary dyskinesia and chronic rhinosinusitis (CRS), and potentially to the inability to fight viral agents that cause the common cold. Some physiological properties of NO include its use as an anti-inflammatory, anticoagulant, and/or antimicrobial agent.

The use of NO in inhalation therapy has also been explored. Inhaled nitric oxide has been used to treat lung failure, and has been shown to enhance pulmonary vasodilation and lower pulmonary vascular resistance. Inhaled nitric oxide has also been approved by the U.S. Food and Drug Administration (FDA) to treat neonates with hypoxic respiratory failure. It has also been shown to improve oxygenation and to reduce the need for extracorporeal membrane oxygenation therapy.

SUMMARY

A moisture or hydrating liquid activatable solid formulation for nitric oxide (NO) generation includes a nitrite source; a copper (I) or copper (II) catalyst; an NO generation accelerant; and a solid pH buffer. The nitrite source is to generate NO when exposed to an effective amount of moisture or a hydrating liquid. The pH buffer is present in an amount sufficient to render a pH of the moisture or hydrating liquid activatable solid formulation from greater than 4 to about 9.0.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear. In some of the drawings (e.g., FIGS. 9-20), data is shown for nitric oxide (NO) release profiles or kinetics (e.g., PPB or PPBV; Y axis) as a function of time (X axis) for compressed pellets of various formulations. In these drawings/figures, the data shows a wide band of values because of the variations associated with uneven hydration of the pellet.

FIG. 1A is a photograph of an example of the NO generating formulation formed into two single pellets, each in a plastic sheath;

FIG. 1B is a photograph of an example of the NO generating formulation formed into a single pellet without a plastic sheath;

FIGS. 2A and 2B are schematic illustrations of an example face mask inhalation device, showing the NO generating formulation-holding housing in an opened position (FIG. 2A) and a closed position (FIG. 2B);

DETAILED DESCRIPTION

Figure 2B:
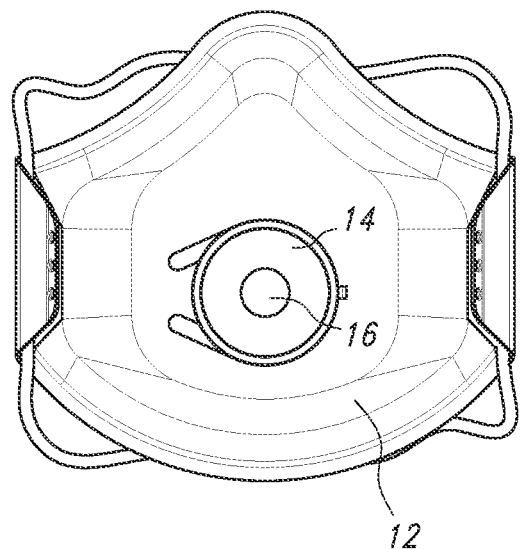

Nitric oxide (NO) is a potent antithrombotic, anti-inflammatory, antibacterial and antiviral agent. NO deficiencies in vivo can either be genetic or polymorphism-related, or induced by pathologies or pathogens that take advantage of upstream regulation of NO production. Deficiencies in NO production can reduce mucociliary function (which is one of the primary innate immune defense mechanisms in the airway epithelium and is also directly correlated with ciliary beat frequency), increase susceptibility to microbial infections, and/or promote persistence of bacterial biofilm that are refractory to antibiotics.

NO inhalation therapy introduces NO into a patient's lungs, and thus can increase mucociliary function, decrease susceptibility to microbial infections, and/or promote resistance of bacterial biofilm. NO has been shown to be effective against SARS-coronavirus, and may be effective at treating other viruses, such as COVID-19, or SARS-CoV-2. The use of inhaled nitric oxide may prove to be beneficial in other areas as well, such as during lung transplants, for treating pulmonary hypertension, as an inhaled antiseptic agent, as well as for treatment of other conditions throughout the body including ischemic stroke, heart attack, thrombosis, and traumatic brain injuries, etc.

Examples of moisture (e.g., water vapor) activated, hydrating liquid activated, or light activated nitric oxide gas generating systems/devices are disclosed herein. In the example devices, nitric oxide (NO) gas is generated on demand from an inhalation device in contact with example(s) of moisture activated, hydrating liquid activated, or light activated NO generating formulations (also referred to herein as NO release formulations).

An example of the NO generating formulation, includes: a stable NO donor/adduct (e.g., an S-nitrosothiol (RSNO) powder or nitroprusside). In addition to the stable NO donor/adduct, some examples of the NO generating formulation further include a binder and an additive. The additive is to control (e.g., accelerate) a rate of release of NO from the stable NO donor/adduct after the formulation is exposed to an effective amount of water vapor, hydrating liquid, or blue or ultraviolet (UV) light.

In some examples, the NO generating formulation is in the form of a solid (e.g., pellets/tablets/disks) including a stable NO donor/adduct (e.g., RSNO (GSNO)), an additive (e.g., an accelerant), and a binder. In some examples, a lubricant and/or an inert material and/or a pH control material may be included. In some other examples, where the NO release formulation is alkaline (e.g., greater than pH 8.5), an additive/accelerant would not be included.

In other examples, the NO generating formulation is in the form of a solid that is moisture activatable or hydrating liquid activatable. This moisture or hydrating liquid activatable solid formulation includes a nitrite source that is to generate NO when exposed to an effective amount of moisture or a hydrating liquid; a copper (I) or copper (II) catalyst; an NO generation accelerant; and a solid pH buffer, wherein a pH of the moisture or hydrating liquid activatable solid formulation ranges from greater than 4 to about 9.0. This solid formulation may also include a binder, a lubricant, a hydration agent, an oxygen scrubber, an $NO_2$ scavenger, a desiccant, and combinations thereof.

In still other examples, the NO generating formulation is in the form of a solution or a dispersion. In some of these examples, any example of the solid formulation disclosed herein is mixed with a hydrating liquid.

"Nitric oxide adducts" (NO adducts) and "NO-donors" refer to compounds and functional groups which, under specific environmental conditions (e.g., moisture, hydration) or when exposed to light of a particular wavelength, can donate and/or release NO. The term "NO-donor/adduct" specifically refers to S-nitrosothiols or nitroprusside. The term "nitrite source" specifically refers to any compound that is a source of nitrite. As such, as used herein, the phrase "moisture activated NO release formulation" includes an NO donor/adduct or nitrite source that is capable of releasing NO gas molecules when exposed to an effective amount of water vapor and/or a hydrating liquid (e.g., water). In an example, a suitable amount of water vapor may be found in conditions ranging from about 40% relative humidity to as much as 100% relative humidity (see. e.g., FIG. 15B).

Similarly, a "light activated NO release formulation" includes an NO donor/adduct that is capable of releasing NO gas molecules when exposed to the particular wavelength or wavelengths of light at varying intensities to generated a desired amount of NO.

Some examples of the NO donor/adduct or the nitrite source disclosed herein can be activated by two or more of moisture, a hydrating liquid, and light.

In some of the examples disclosed herein, an example of the nitric oxide generating formulation is specifically formulated in, for example, a solid form (e.g., a powder formulation or a single solid or single densely packed solid mass using pressure (e.g., about 25-50 kn), e.g., a pellet, tablet or disk) that, when exposed to humidified air (such as from the inhaled/exhaled breath of a user; from an air humidifier; etc.) will generate gaseous NO over a wide range (from about 50 ppbv to greater than about 50,000 ppbv) that covers the range that has been demonstrated to be therapeutically effective for inhalation therapy. The powder formulation may be granular in nature. "Densely packed," as used herein, means not granular in nature, similar to the density of a crystalline material. The NO generating formulation allows for the spontaneous delivery of NO during a prolonged period in which the user is in contact with the example inhalation device including the moisture activated NO release formulation.

In other of the examples disclosed herein, the nitric oxide generating formulation is in a solid form (pellet, table, disk, or powder form) and is contained within a container that can be affixed to, or otherwise introduced to an inhalation device. In some instances, the container is permeable to humidified air and to NO. This type of container enables the humidified air to enter into contact with the nitric oxide generating formulation, and also enables generated gaseous NO to be released from the container. In other instances, the container is transparent to visible blue and/or cyan light (wavelengths ranging from about 400 nm to about 490 nm and/or from about 490 nm to about 520 nm) and/or ultraviolet light (wavelengths ranging from about 10 nm to about 400 nm) and is permeable to NO. This type of container enables the light to enter into contact with the nitric oxide generating formulation, and also enables generated gaseous NO to be released from the container.

In other of the examples disclosed herein, the nitric oxide generating formulation is a solid or powdered form sealed in a package that prevents moisture from reaching the nitric oxide generating formulation until NO generation is desired. In some instances, the package is opened and the contents are exposed to outside humidity for NO generation. In other instances, the package is opened and the contents are reconstituted in a liquid which is poured into a reservoir, such as the one shown in FIG. 25B.

Figure 25A:
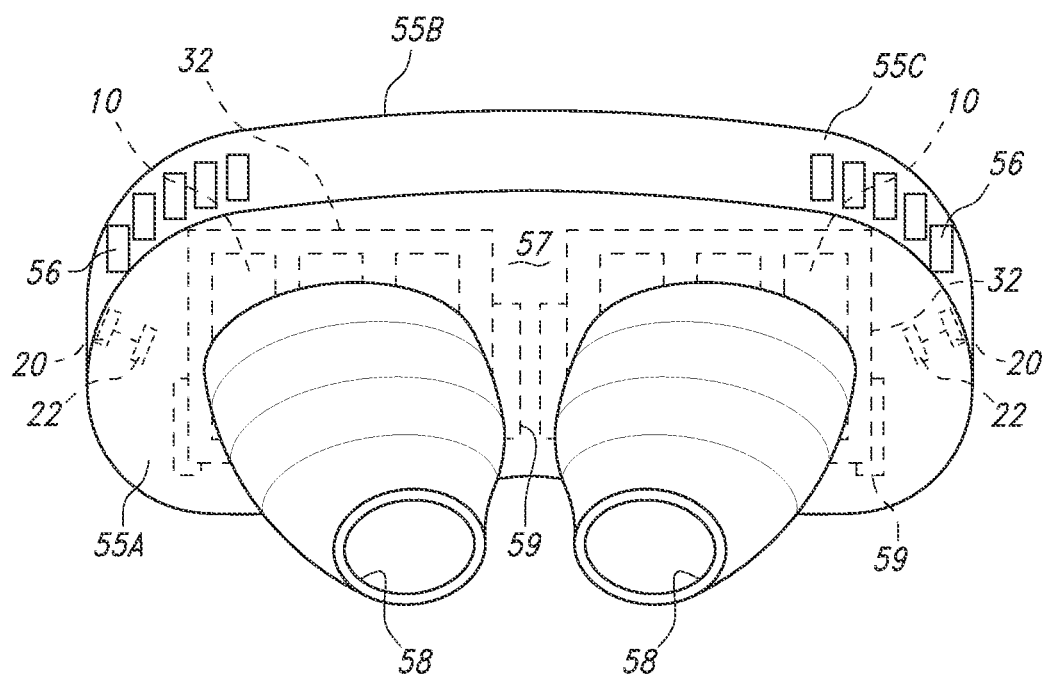
FIG. 25A is a perspective and schematic illustration of a nose vent plug including a solid form of the NO generating formulation therein.
Figure 25B:
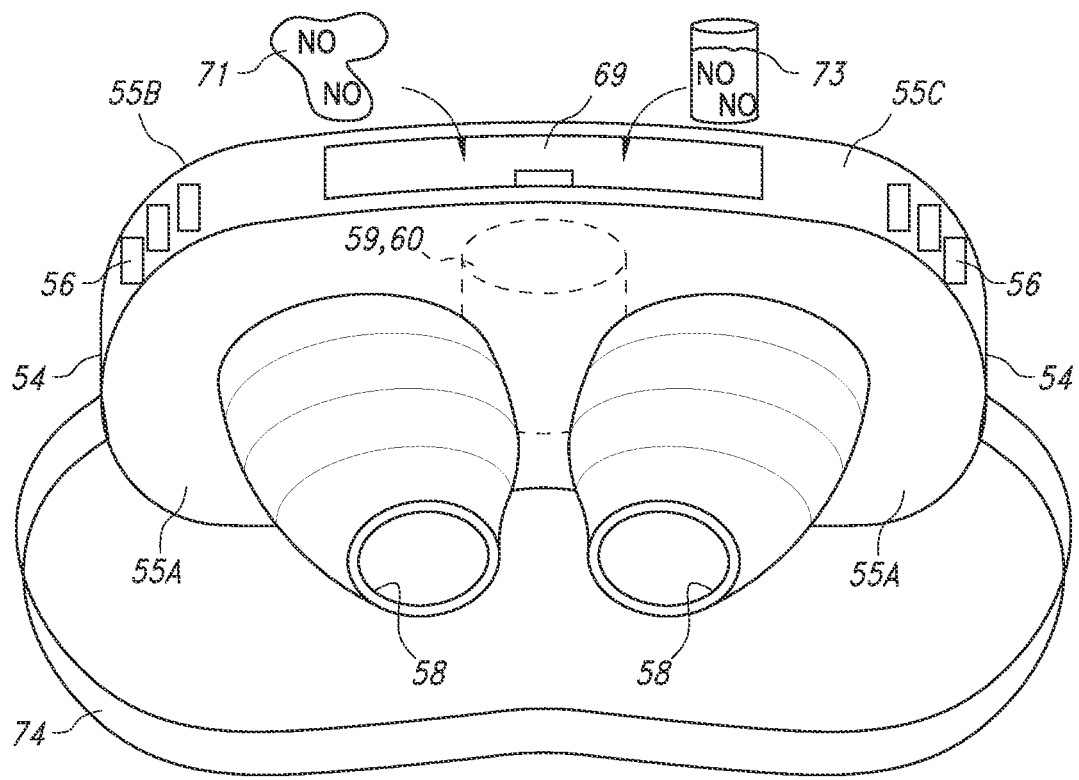
FIG. 25B is a perspective and schematic illustration of a nose vent plug including a reservoir to receive a liquid form of the NO generating formulation therein.

In still other examples disclosed herein, the nitric oxide generating formulation is a coating or powder that is added to an absorbent pad (e.g., PIG® absorbent pad) and placed into a device such as the one described in FIG. 25B, which generates NO when humidity or liquid is added to the device.

The systems/devices disclosed herein are relatively compact and eliminate the need for nitric oxide tanks (i.e., NO in compressed gas cylinders), which simplifies the systems/devices and reduces the cost of the systems/devices.

Use of examples of the NO release formulation disclosed herein to produce inhaled nitric oxide may prove efficacious for combating, including prophylactic use, and/or reducing infectious agents (e.g., viruses, bacteria, fungi), treating lung failure, enhancing pulmonary vasodilation, and lowering pulmonary vascular resistance and other conditions that involve inflammation, coagulation and infection. As mentioned above, inhaled nitric oxide may also be used to treat neonates with hypoxic respiratory failure, and may improve oxygenation and reduce the need for extracorporeal membrane oxygenation therapy. Use of examples of the NO release formulation disclosed herein to produce inhaled nitric oxide may also prove to be beneficial in other areas as well, such as during lung transplants, for treating pulmonary hypertension, as an inhaled antiseptic agent, for disinfecting of air, etc.

For example, use of examples of the NO release formulation disclosed herein may generally increase NO levels outside and within epithelial cells and immune cells, which can also help control ciliary beat frequency. As such, the example nitric oxide generating formulation described herein may help to restore/enhance mucociliary function (which, as noted above, is directly correlated with ciliary beat frequency). Restored/enhanced mucociliary function may increase the defense against chronically colonized pathogens and reduce, or even prevent, disease perpetuation. In addition, the released nitric oxide from the NO release formulation will have direct bactericidal, antiviral and antifungal activity on most types of bacteria, viruses and fungi that can infect the sinonasal cavities and other parts of the respiratory system. Therefore, this example nitric oxide generating formulation may be beneficial for treating or even preventing airway infections, including upper airway infections such as CRS.

NO Generating Formulations

Two examples of solid formulations for NO generation are disclosed herein. The first solid formulation may be moisture, hydrating liquid, and/or light activated, and includes the NO donor/adduct disclosed herein. The second solid formulation may be moisture and/or hydrating liquid activated, and includes the nitrite source disclosed herein.

First Solid Formulation

Some examples of the NO generating formulation include a stable NO donor/adduct. These formulations may be referred to herein as the first solid formulation. In some instances, these examples of the NO generating formulation include the stable NO donor/adduct; a binder; and an additive. Examples of the moisture activated stable NO donor/adducts include, e.g., an S-nitrosothiol (RSNO) powder or nitroprusside.

The moisture activated RSNO that is selected for the nitric oxide generating formulation is a species that is naturally occurring in the human body or another organism, or is capable of decomposing to a species that is naturally occurring in the human body, or is a drug that is suitable for human use (e.g., ingestion, consumption, etc.). In any of the examples disclosed herein, the moisture activated RSNO or RSNO powder is selected from the group consisting of S-nitrosoglutathione (GSNO, naturally occurring in the human body), S-nitroso-cysteine (CYSNO, naturally occurring in the human body), S-nitroso-N-acetyl-penicillamine (SNAP, decomposes to the drug, penicillamine), S-nitroso-penicillamine, and S-nitroso-albumin (naturally occurring in vertebrate animals).

S-nitrosoglutathione (GSNO) is one example of the NO releasing S-nitrosothiol (RSNO) molecule. GSNO exists in the human body as a result of NO (generated by endothelial cells, macrophages, sinus epithelial cells, etc.) reacting with oxygen to form $N_2O_3$, which can provide a nitrosonium ion ($NO^+$) to react with the thiol group of glutathione to form GSNO. As such, the use of GSNO in the nitric oxide generating formulation disclosed herein does not introduce any foreign or toxic agents into the nasal cavity/airways.

GSNO may be prepared from glutathione (GSH) by acidifying a mixture of sodium nitrite/GSH with hydrochloric acid and then isolating the GSNO species (as solid crystals). Alternatively, the GSNO may be a commercially available sample.

In some examples, moisture activated S-nitrosothiol (RSNO) molecules other than GSNO may be used in the nitric oxide generating formulation. Examples of these other S-nitrosothiols include S-nitroso-cysteine (CYSNO, naturally occurring in the human body), S-nitroso-N-acetyl-penicillamine (SNAP, decomposes to the drug, penicillamine), S-nitroso-penicillamine, and S-nitroso-albumin (naturally occurring in the human body).

In an example of the moisture activated or hydrating liquid activated first solid formulation, the RSNO powder is selected from the group consisting of S-nitrosoglutathione (GSNO), S-nitroso-cysteine, S-nitroso-N-acetyl-penicillamine, S-nitroso-penicillamine, and S-nitroso-albumin.

In a further example of the moisture activated or hydrating liquid activated first solid formulation, the stable NO donor/adduct is nitroprusside.

Some examples of the S-nitrosothiols are also light activated/sensitive. Examples of the light activated/sensitive S-nitrosothiols include S-nitroso-N-acetyl-penicillamine (SNAP) crystals, S-nitrosoglutathione (GSNO) crystals, and combinations thereof.

In examples of the first solid NO generating formulations of the present disclosure, it is to be understood that one or more hydrophilic or hydrophobic materials may be used as the binder. Some examples include polyvinyl alcohol (PVA), polyvinyl acetate (PVAc), poly(ethylene glycol) (PEG), polyacrylamide, acetates, polyethylene oxide (PEO), poly ethyl acrylate (PEA), polyvinyl pyrrolidone (PVP), untreated or treated polypropylene, polyimide, polyamide, polystyrene, poly(vinyl chloride), polyacrylonitrile, and variations thereof (e.g., polyvinyl pyrrolidone-vinyl acetate (PVP-VA)), e.g., as a physical blend or admixture wherein each polymer maintains its unique chemical nature. Hydrophilic materials may be selected as the binder when it is desirable to improve the water or moisture uptake capabilities of the NO generating formulation. While some hydrophilic material have been listed, any of a variety of other hydrophilic polymers may also be used, such as, polysaccharides (e.g., cellulose, hydroxypropyl cellulose (HPC), hydroxypropyl methylcellulose (HPMC), microcrystalline cellulose, chitin, callose, chitosan, arabinoxylans, pectin, glucan, etc.), starch (e.g., corn, potato, wheat, etc.), lactose, glycosaminoglycans (e.g., hyaluronic acid/hyaluronate, heparin, chondroitin sulfate. keratan sulfate, etc.), and/or combinations thereof. It is contemplated as being within the purview of the present disclosure that any of a variety or combination of polymers/copolymers or other hydrophilic or hydrophobic materials may be used to yield a binder with desired properties.

In an example, the weight average molecular weight of the binder material used may be from about 5000 Mw to about 500,000 Mw; or from about 10,000 Mw to about 200,000 Mw.

In an example, the hydrophilic binder is selected from the group consisting of polyvinyl acetate (PVAc), poly(ethylene glycol) (PEG), polyacrylamide, acetates, polyethylene oxide (PEO), poly ethyl acrylate (PEA), polyvinylpyrrolidone (PVP), polyvinyl pyrrolidone-vinyl acetate (PVP-VA), hydroxypropyl cellulose (HPC), hydroxypropyl methylcellulose (HPMC), microcrystalline cellulose, corn starch, and combinations thereof. In another example, the hydrophobic binder is selected from the group consisting of untreated polypropylene, polystyrene, poly(vinyl chloride), and polyacrylonitrile.

In the first solid formulation, the NO generation additive that is selected is capable of controlling the rate of release of nitric oxide from the NO donor/adduct after the formulation is exposed to an effective amount of water vapor (moisture), hydrating liquid, or light. The inclusion of the additive in the formulation enables control over the time profile of NO release, which may enhance the antimicrobial activity and/or therapeutic benefit. In some instances, the additive accelerates the release rate of the nitric oxide. In an example of the first solid formulation, a ratio (mol/mol) of the NO donor/adduct to the additive ranges from 1:0.5 to 1:10.

It is to be understood that the additive (also referred to herein as an NO generation accelerant) may be a reducing agent (that reduces the NO donor/adduct) and/or may be a catalyst (that accelerates the reduction of the NO donor/adduct). In an example, the NO generation accelerant is selected from the group consisting of ascorbate sources, tocopherols and tocotrienols, those based on sulfur, thiol, or thiolate, those based on boron, silanes, those based on phosphine, hydride donors, metal based complexes, metal based agents, nitrogen based agents, and carbon based complexes.

Examples of suitable ascorbate sources include ascorbic acid, sodium ascorbate, potassium ascorbate, calcium ascorbate, magnesium ascorbate, ascorbyl palmitate, ascorbyl stearate, ascorbyl oleate, ascorbyl linoleate, ascorbyl glucoside, ascorbyl phosphate, or any other ascorbate source that can accelerate the release rate of the nitric oxide.

Tocopherols and tocotrienols are vitamin E nutrients and analogues thereof. Examples of suitable tocopherols and tocotrienols for use as the NO generation accelerant include alpha-tocopherol, beta-tocopherol, gamma-tocopherol, delta-tocopherol, alpha-tocotrienol, beta-tocotrienol, gamma-tocotrienol, delta-tocotrienol, or any other tocopherol or tocotrienol that can accelerate the release rate of the nitric oxide.

Examples of NO generation accelerants based on sulfur, thiol, or thiolate include cysteines, acetylcysteines, alkyl thiols and thiolates (e.g., ethanethiol, sodium ethanethiolate, cyclohexanethiol, sodium 2-propanethiolate, etc.), thiophenols/thiophenolates (e.g., benzenethiol, sodium benzenethiolate, lithium thiophenolate, 4-methylbenzenethiol, etc.), triphenylmethyl mercaptans, dithiothreitol, mercaptoethanol, dithionates, thiosulfates, hydrogen sulfides, sodium sulfide, potassium sulfide, or any other sulfur, thiol, or thiolate based component that can accelerate the release rate of the nitric oxide.

Examples of NO generation accelerants based on boron include borohydrides (e.g., sodium borohydride, lithium borohydride, lithium triethylborohydride, etc.), diborane, other boranes, such as alpine-borane, disiamylborane, thexyl borane, catecholborane, etc., (R)-2-Methyl-CBS-oxazaborolidine, or any other boron based component that can accelerate the release rate of the nitric oxide.

Examples of suitable silanes include triethylsilane, triisopropylsilane, phenylsilanes, diphenylsilanes, or any other silane that can accelerate the release rate of the nitric oxide.

Examples of NO generation accelerants based on phosphine include phosphine, diphosphane, trialkyl phosphines (e.g., tributylphosine, etc.), triphenyl phosphines, tris(2-carboxyethyl)phosphine, or any other phosphine that can accelerate the release rate of the nitric oxide.

Examples of suitable hydride donors include nicotinamide adenine dinucleotide (NADH) and analogs thereof, nicotinamide adenine dinucleotide phosphate (NADPH) and analogs thereof, flavin adenine dinucleotide ($FADH_2$ or FADH) and analogs thereof, or any other hydride donor that can accelerate the release rate of the nitric oxide.

Examples of suitable metal based complexes include ferrocyanide, ferrocenium, cobaltocene, tin(II) chloride, tributyltin hydride, titanium chloride, lithium hydride, lithium aluminum hydrides, sodium hydride, tris(bipyridine)

ruthenium complexes, or other metal based complex that can accelerate the release rate of the nitric oxide.

Some examples of other metal based agents suitable for use as the NO generation accelerant include lithium, sodium, potassium, aluminum powder/dust, iron powder/dust, zinc powder/dust, copper powder, silver powder, sodium amalgam, copper ions, zinc ions, or zinc oxide particles. Some transition metal salts and ligand complexes may be used as the metal based agent. For example, iron salts (e.g., iron chloride, iron nitrate, iron triflate, iron oxides, etc.), iron heme (e.g., iron tetraphenyl porphyrin, iron octaethylporphyrin, iron protoporphyrin IX, etc.) and non-heme complexes (e.g., iron tris(2-methylpyridynl) amines, etc.) may be suitable NO generation accelerants. For another example, cobalt, manganese, nickel, vanadium, etc., salts, porphyrins, and other ligand complexes may be suitable NO generation accelerants. For still another example, palladium, platinum, silver, gold, ruthenium, rhodium, osmium, iridium, molybdenum, etc. salts, complexes, nanoparticles and alloys may be suitable NO generation accelerants.

Examples of suitable nitrogen based agents include ammonia, hydrazine, hydroxylamine, or any other nitrogen based agent that can accelerate the release rate of the nitric oxide.

Examples of suitable carbon based complexes include carbon black, graphites (e.g., potassium graphite ($KC_8$, $KC_{24}$, and other variants), or any other carbon based complex that can accelerate the release rate of the nitric oxide.

For any of the NO generation accelerants, it is believed that any oxidation state, salt (e.g., counter ion variant, such as sodium, potassium, magnesium, calcium, etc.), hydration state (e.g., monohydrate, dihydrate, trihydrate, hemi(penta-hydrate), hemihydrate, etc.), protonation state, or combinations thereof may be used.

In an example of the first solid NO generating formulation, the additive is selected from the group consisting of reduced glutathione, cysteine, ascorbic acid or ascorbate, ascorbyl palmitate, copper ions, zinc ions, zinc oxide particles, an organoselenium species, and combinations thereof. In an example, the organoselenium species is selected from the group consisting of selenocysteine and ebeselen. An example of a combination of additives is reduced glutathione and ascorbate.

The following are some examples of how the additive can control or accelerate the rate of release of nitric oxide from RSNO, and in particular, from GSNO. Glutathione can increase the NO release rate from GSNO via the formation of an initial N-hydroxysulfenamide species (e.g., GS-N(OH)-SG), which then converts to a radical $GS^-$ that can react with another GSNO molecule to liberate NO and form the GSSG disulfide species. Cysteine is able to transnitrosate with GSNO to form CysNO, which releases NO much faster than GSNO. Ascorbic acid or ascorbate can readily oxidize to form smaller threose structures (3 carbon sugars). The spontaneous oxidation of ascorbate can be coupled with reduction of GSNO to liberate NO plus GSH. Further, the oxidation products of ascorbate, i.e., the smaller threose structures, are also reducing agents that can provide electron(s) to GSNO, and thus may also contribute to the direct reduction of the GSNO to NO. In an example, the ascorbic acid or ascorbate may be allowed to oxidize in a solution for up to 5 days, dried, and then incorporated into the nitric oxide generating formulation. An organoselenium species can catalyze NO generation from GSNO. Copper or zinc ions may be reduced to their +1 oxidation state by any trace free thiols that exist in the GSH formulation, and the Cu(I) or Zn(I) ions can then reduce the GSNO to NO and GSH.

In an example, the first solid NO generating formulation further includes a lubricant. When included, an example of the lubricant is selected from the group consisting of stearic acid, palmitic acid, sodium stearate, zinc stearate, magnesium stearate, calcium stearate, sodium laurate, zinc laurate, sodium palmitate, zinc palmitate, ascorbyl palmitate, sodium oleate, sodium myristate, sodium dodecanoate, and combinations thereof. Other suitable lubricants include alkyl alcohols, such as octadecanol, sodium octadecan-1-olate, stearyl alcohols, dodecanol, cis-9-octadecen-1-ol, etc. Still other suitable lubricants include alkyl amines, such as oleylamines, octadecylamine (stearamine), octadecylamine hydrochloride, hexadecylamine, etc. It is to be understood that the lubricant is not necessary for the generation of NO; however, in some examples, the lubricant may make the pellet more robust and may modify (slow) NO release kinetics. However, if the solid/pellet is compressed at high enough pressure (e.g., greater than 40 kn), the pellet without lubricant should stay together (although the resultant NO release may in some instances be slower as the press pressure used increases). When the solid formulation is in powder form, the lubricant may improve the flowability of the dry powder. Improved flowability can render the powder better suited for handling and processing (e.g., being loaded into a pouch, a sachet, or a reservoir via a filling machine).

In an example, the first solid NO generating formulation further includes a hydration agent. A hydration agent may be particular suitable for use with any of the moisture activatable or the hydrating liquid activatable NO donor/adducts of the first solid formulation, as the hydration agent can increase moisture and/or hydrating liquid uptake and, in turn, NO release. In an example, the hydration agent is an akali or alkaline-earth metal halide, an akali or alkaline-earth metal nitrate, an akali or alkaline-earth metal acetate, an akali or alkaline-earth metal hydroxide, an ammonium halide, ammonium acetate, or another metal salt.

Examples of akali and alkaline-earth metal halides include magnesium chlorides, calcium chloride, sodium chloride, potassium chloride, lithium chloride, magnesium bromide, magnesium iodide, magnesium fluoride, sodium bromide, etc. Examples of akali and alkaline-earth metal nitrates include sodium nitrate, potassium nitrate, calcium nitrate, magnesium nitrate, etc. Examples of akali and alkaline-earth metal acetates include sodium acetate, potassium acetate, calcium acetate, magnesium acetate, etc. Examples of akali and alkaline-earth metal hydroxides include sodium hydroxide, potassium hydroxide, calcium hydroxide, magnesium hydroxide, etc. Examples of ammonium halides include ammonium chloride, ammonium bromide, etc. Other metal salts, such as aluminum acetate, aluminum chloride, aluminum nitrate, zinc acetate, zinc chloride, zinc nitrate, tin chloride, etc. may also be used.

In an example, the first solid formulation for NO generation further includes a desiccant. A desiccant may be desirable to keep any of the solid formulations stable until moisture or hydrating liquid exposure. While any suitable desiccant may be used, some examples include silicon dioxide, silica gels, colloidal silicas/silicon dioxides, fumed silica/silicon dioxides, alumina, and other aluminum oxides.

It is to be understood that the components of the first solid NO generating formulation including the NO donor/adduct may be present in any desired suitable amounts. As such, the NO donor/adduct, the binder, the lubricant, and the NO generation additive may be present in any desired suitable amount. However, in an example, the stable NO donor/adduct (e.g., an S-nitrosothiol (RSNO) powder) is present in an amount ranging from about 1 wt % to about 50 wt %, or from about 1 wt % to about 30 wt %, or from about 3 wt % to about 12 wt % of the first solid NO generating formulation; the binder is present in an amount ranging from greater than 0 wt % to about 90 wt %, or from greater than 0 wt % to about 82 wt %, or from about 15 wt % to about 82 wt %, or from about 25 wt % to about 82 wt % of the first solid NO generating formulation; the lubricant (when present in the formulation) is present in an amount ranging from greater than about 0 wt % to about 90 wt %, or from about 0.1 wt % to about 75 wt %, or from about 1 wt % to about 15 wt % of the first solid NO generating formulation; and the additive is present in an amount ranging from about 0.5 wt % to about 70 wt %, or from about 1 wt % to about 60 wt %, or from about 3 wt % to about 60 wt % of the first solid NO generating formulation. When zinc oxide particles are utilized as the NO generation additive, they may be present in an amount ranging from about 1 wt % to about 90 wt % of the first solid NO generating formulation. When included in this first example of the solid formulation, the hydration agent may be present in an amount ranging from about 0.1 wt % to about 50 wt % of a total weight of the first solid NO generating formulation. The desiccant may be present in an amount ranging from about 0.1 wt % to about 30 wt % of a total weight of the first solid NO generating formulation.

In another example, the first solid formulation including the NO donor/adduct is made alkaline (e.g., greater than pH 8.5) by addition of an alkaline material. In this example, an additive/accelerant would not be included. If the pH is high (greater than about 8.5), the GSNO is unstable, and NO is liberated even without an additive/accelerant. Examples of the alkaline material are selected from the group consisting of sodium carbonate, a mixture of sodium carbonate and sodium bicarbonate, sodium hydroxide, potassium hydroxide, disodium hydrogen phosphate, trisodium phosphate, fully deprotonated forms of pyrophosphate (e.g., tetrasodium pyrophosphate, tetrapotassium pyrophosphate, etc.), ethanolamine, taurine, borate buffers, and combinations thereof.

In an example, the first solid NO generating formulation (including the NO donor/adduct) further includes an inert material. When the inert material is included in the formulation, it is present in an amount ranging from greater than about 0 wt % to about 50 wt %, or from about 5 wt % to about 25 wt % of the NO generating formulation. As used herein, "inert material" means a material that does not greatly influence NO release (i.e., a material that causes less than a 10% change in the rate of NO release). In the examples disclosed herein, the inert material may act, e.g., as an anticaking agent, a bulking agent, and/or a binder (though it is to be understood that an inert material binder is not involved in water uptake as is the hydrophilic binder). In one example, the inert material is sodium bicarbonate. Some of the other components, e.g., lubricants, desiccants, etc., included in the solid formulations may also be considered inert materials because they do not greatly influence NO release.

In an example, the first solid NO generating formulation (including the NO donor/adduct) further includes a pH control material. It is to be understood that any suitable pH control material may be used, and that the pH control material is present in the first solid formulation an amount sufficient to render the pH greater than 9.5. In an example, the pH control material is selected from the group consisting of a sodium phosphate buffer (e.g., phosphate buffered saline (PBS)), a potassium phosphate buffer, and combinations thereof. Other suitable pH control materials include carbonate salts, other phosphate salts, or any other buffering material that does not react with nitric oxide.

Some examples of the first solid NO generating formulation (including the NO donor/adduct) further include an absorbent to scavenge nitrogen dioxide ($NO_2$) released by the NO generating formulation, a reagent to convert generated $NO_2$ back to NO, or combinations thereof. $NO_2$ can be generated by the reaction of $O_2$ with NO, and can be toxic to the recipient/patient. Therefore, it is desirable to remove any generated $NO_2$, to convert any generated $NO_2$ back to NO or to maintain very low levels of $NO_2$ breathed in by the user. A soda lime scrubber may be included as an absorbent. If the $NO_2$ content is greater than 1-3 ppm in the final gas phase, the soda lime scrubber can be used to remove the excess $NO_2$. An example of a reagent or catalyst that can convert generated $NO_2$ back to NO is ascorbic acid impregnated silica particles.

In an alternate example, for example when a deliquescent salt (e.g., calcium chloride) is used, the first solid NO generating formulation including the NO donor/adduct may be a two-part system. The use of a very hydrophilic material (e.g., the deliquescent salt such as calcium chloride) increases NO production, since the pellet at least partially dissolves, thus behaving like a solution. In these examples, the deliquescent salt may be added to the first solid NO generating formulation when NO generation is desirable.

The first solid formulation is a moisture, hydrating liquid, or light activated NO generating formulation that includes the NO donor/adduct. The first solid formulation may be in the form of a powder.

The first solid formulation including the NO donor/adduct may also be applied as a coating or film to a surface, using an adhesive that does not interfere with NO generation.

In still other examples, the first solid formulation may be molded/formed/pressed, etc. into a solid of any suitable shape or size, e.g., pellets, tablets, disks, etc. In some examples, the formed solid may be up to about 50 mm diameter× about 25 mm thickness. In an example, the formed solid is about 5 mm diameter×25 mm long. Beyond a size of 50 mm×25 mm may in some instances not be desirable since surface to volume ratio is a criterion to consider, along with propensity for water uptake. The formed solid may weigh from about 0.1 grams to about 5.0 grams; or from about 0.2 grams to about 0.5 grams.

Examples of the first solid formulation are shown in FIG. 1A and FIG. 1B at reference numerals 10, 10' in the form of solid pellets. The reference numerals 10, 10' are generally used for the NO generating formulation, and it is to be understood that this encompasses any example of the solid formulation disclosed herein. In an example, the NO generating formulation 10, 10' comprises a single formed solid (i.e., each of the components (e.g., RSNO, binder, additive) of the first solid formulation is present in a single pellet as opposed to a two-part system). FIG. 1A shows an example of the NO generating formulation 10, which is in the form of two formed single pellets, each of which includes a plastic sheath (which may be added when desired for mechanical rigidity to reduce pellet fragility). In an example, the plastic sheath is polyethylene. An example method of making the sheath is inserting a formed pellet into polyethylene, then puncturing the sheath with a needle to fix the pellet in place. The sheath may be any suitable thickness as desired, e.g., about 150 μm thick. FIG. 1B shows another example of the NO generating formulation 10', which is in the form of a single pellet formed without a plastic sheath.

It is to be understood that, in use with examples of the container and/or the inhalation device, one or a plurality of the single pellets may be used to provide the desired amount of gaseous NO.

In some examples, the first solid formulation may be maintained in sealed packaging until it is desirable to expose the formulation to moisture to generate NO. In other examples, the first solid formulation may be shielded from light until it is desirable to expose the formulation to light to generate NO. In still other examples, the first solid NO generating formulation including the NO donor/adduct may be re-constituted in a hydrating liquid, such as deionized or purified water, to generate one example of the liquid form of the NO generating formulation.

Second Solid Formulation

Instead of the NO donor/adduct as defined herein, other examples of the solid NO generating formulation include a nitrite source that generates NO molecules upon exposure to moisture or a hydrating liquid. The nitrite source may be maintained in a solid form (e.g., a powder, pellet, etc.) until it is desirable to generate NO.

This second solid (e.g., powder) formulation for NO generation may include the nitrite source, a copper (I) or (II) catalyst, an additive (i.e., the NO generation accelerant), and a pH buffer. This second solid formulation may also include a binder, a lubricant, a hydration agent, an oxygen scrubber, an $NO_2$ scavenger, a desiccant, and combinations thereof. The nitrite source, the copper (I) or (II) catalyst, the NO generation additive, and the pH buffer, alone or with any combination of the other components, may be mixed together and placed into a housing reservoir, a pouch, a sachet, or another suitable container.

The nitrite source is selected from the group consisting of ammonium nitrites, alkyl nitrites, dicyclohexylamine nitrite, phosphazine nitrites, and nitrite salts.

Examples of suitable ammonium nitrites include ammonium nitrite or tetrabutylammonium nitrite. Examples of suitable alkyl nitrites include methyl nitrites, ethyl nitrites, butyl nitrites, isoamyl nitrites, isopentyl nitrites, etc. An example of a suitable phosphazine nitrite includes bis(triphenylphosphine)iminium nitrite). The nitrite salt may be any water soluble, inorganic nitrite salt. Some example water soluble, inorganic nitrite salts include alkali metal and alkaline earth metal nitrite salts or transition metal nitrite salts. Specific examples include nitrite salts of Li (lithium), Na (sodium), K (potassium), Rb (rubidium), Ca (calcium), Mg (magnesium), Cu (copper), Zn (zinc), Ag (silver), Au (gold), Fe (iron), Co (cobalt) (e.g., hexanitrocobaltate), Mn (manganese), Ti (titanium), etc. Most other metal salts are also soluble in water, for example, Al (aluminum) salts, Pb (lead) salts, and Sn (tin) salts, etc. One specific example of the nitrite salt is sodium nitrite ($NaNO_2$). The nitrite salt may be acidified when exposed to moisture or a hydrating liquid which generates nitrous acid in situ, which in turn, may be reduced to generate the NO.

The nitrite source may be present in the second solid formulation in an amount up to 80 wt % based on the total weight of the second solid formulation.

This second example of the solid formulation for NO generation also includes the copper (I) or copper (II) catalyst. The copper (I) or copper (II) catalyst is selected from the group consisting of copper salts, copper oxides, copper hydroxides, copper hydrates, copper sulfides, copper selenides, copper pyrophosphates, copper phosphates, copper selenites, copper carboxylates, copper acetonitriles, copper acrylates, copper thiolates, copper dithiolates, organo-copper compounds, copper alkyl-oxides, copper phosphines, solid phase copper complexes, copper ligand complexes, and combinations thereof.

Examples of suitable copper salts cupric nitrate, cupric chloride, cupric bromide, cuprous iodide, copper fluoride, cupric sulfate, copper carbonates, copper perchlorates, copper tetrafluoroborate, copper citrates, and copper ammonium salts. Some examples of suitable copper ammonium salts include ammonium copper chloride, ammonium copper sulfate, etc.

Examples of suitable copper carboxylates include cupric acetate, copper formate, copper trifluoroacetate, copper benzoates, copper phthalic acid/phthalate, copper butyrates, copper ethylhexanoate, copper heptadecanoate palmitate, copper 2-pyrazinecarboxylate, copper thiophenecarboxylate, or any other copper carboxylate that catalyzes the reduction of nitrite to nitric oxide.

An example of a suitable copper acetonitrile is tetrakis (acetonitrile)copper hexafluorophosphate. Other copper acetonitriles may also be used.

Examples of suitable copper acrylates include copper methacrylate, copper ethylacetoacetate, or any other copper acrylate that catalyzes the reduction of nitrite to nitric oxide.

Examples of suitable copper thiolates include copper cysteinate, copper glutathione, thiophenolate, or any other copper thiolate that catalyzes the reduction of nitrite to nitric oxide.

An example of a copper dithiolate is copper benzene-1, 2-dithiolate. Other copper dithiolates may also be used.

Some examples of organo-copper compounds that may be used as the catalyst include copper trifluoromethanesulfonate, copper tosylate, copper bis(heptafluoro-dimethyloctanedionate), copper hydroxyquinoline, copper 2-(1-hydroxyethylidene)-1-cyclopentanone, copper bis(trifluoromethanesulfonyl)imide, copper undecylenate, copper catechol/catecholates, copper phenolates, copper thiophenolates, copper gluconate, copper 3,5-diisopropylsalicylate, copper cyclohexanebutyrate, copper ethylacetoacetate, copper acetylacetonate, copper trifluoroacetylacetonate, copper hexafluoroacetylacetonate, copper tartrate, copper tert-butylacetoacetate, copper (1,10-phenanthroline), tetrakis(pyridine)copper triflate, copper bis[benzothiazolyl phenolato], copper di(naphthoate), copper N-pyruvylideneglycinato, copper alpha-(2-pyridylimino)-o-cresol, copper oxalate, copper bis(8-quinolinolato), copper bis(hexafluoroacetylacetonato), copper aspartate, or any other organo-copper compound that catalyzes the reduction of nitrite to nitric oxide.

Some examples of suitable copper alkyl-oxides include copper methoxide, copper ethoxide, copper butoxide, copper isopropxide, or any other copper alkyl-oxide that catalyzes the reduction of nitrite to nitric oxide.

Some suitable copper phosphines include copper bis (triphenylphosphine), copper bis(triethylphosphine), or any other copper phosphine that catalyzes the reduction of nitrite to nitric oxide.

Solid phase copper complexes may also be used as the copper(I) or copper(II) catalyst. Some examples include copper nanoparticles, copper on silica, copper on carbon, copper doped graphene, copper doped graphite, or any other solid phase copper complex that catalyzes the reduction of nitrite to nitric oxide.

Suitable examples of the copper ligand complex include copper triazacyclononane type complexes (e.g., copper 1,4, 7-triazacyclononane, copper 1,4,7-trimethyl-1,4,7-triazacyclononane, copper 1,4,7-triethyl-1,4-7-triazacyclononane, copper 1,4,7-triisopropyl-1,4,7-triazacyclononane, etc.), copper triazecanes (e.g., 1,4,7-trimethyl-1,4,7-triazecane, etc.), copper ethylenediamines (e.g., copper bis(ethylenediamine)), copper bis(1,3-propanediamine), copper(ethylenediaminetetraacetic acid), copper tetramethylethylenediamine (TMEDA), copper pentamethyldiethylenetriamine (PMDTA), copper ionophores, copper phthalocyanines, copper naphthalocyanines, copper porphyrins, copper corrins, copper chlorophyllins, copper tetraazacyclotetradecanes, copper tris(2-methylpyridynl)amines, copper bis(2-methylpyridyl)amine carboxylates bis(2-methylpyridyl)aminepropionate, bis(2-methylpyridyl)aminebutylate, etc.) copper bis(2-ethylpyridyl)amine carboxylates (e.g., bis(2-ethylpyridyl)aminepropionate, bis(2-ethylpyridyl)aminebutylate, etc.), copper bis[(2-pyridyl)methyl]-2-(2-pyridyl)ethylamine, copper bis[2-(2-pyridyl)ethyl]-(2-pyridyl) methylamine, copper 3-((2-pyridyl)methyl-2-(2-pyridyl) ethylamine)carboxylates (e.g., 3-((2-pyridyl)methyl-2-(2-pyridyl)ethylamine)propanoate), 3-((2-pyridyl)methyl-2-(2-pyridyl)ethylamine) butylate), etc.), copper tri(2-aminoethyl)amines (e.g., copper tri(2-dimethylamino) ethylamine, tri(2-diethylamino)ethylamine, etc.), copper pyrithiones, copper picolinates, copper dithiocarbamates (e.g., dimethyldithiocarbamate, copper diethyldithiocarbamate, copper dibutyldithiocarbamate, etc.), copper imidazoles, copper pyridines, and any other copper(I) (Cu(I)) or copper (II) (Cu(II)) complex that catalyzes the reduction of nitrite to nitric oxide.

For any of the copper catalysts, it is believed that any oxidation state, salt (e.g., counter ion variant, such as sodium, potassium, magnesium, calcium, etc.), hydration state (e.g., monohydrate, dihydrate, trihydrate, hemi(pentahydrate), hemihydrate, etc.), protonation state, or combinations thereof may be used. For example, any of the listed complexes may be used in the Cu(II) or Cu(II) oxidation state.

The copper catalyst may be present in the second solid formulation in an amount ranging from about 0.1 wt % to about 50 wt % based on the total weight of the second solid formulation.

The second solid formulation also includes the NO generation additive. In the second solid formulation, the NO generation additive that is selected is capable of controlling the rate of release of nitric oxide from the nitrite source after the formulation is exposed to an effective amount of water vapor or hydrating liquid. It is to be understood that the NO generation accelerator may be a reducing agent (that reduces the nitrite source) and/or may be a catalyst (that accelerates the reduction of the nitrite source). In an example of the second solid formulation, a ratio (mol/mol) of the nitrite source to the NO generation additive ranges from 1:0.5 to 1:10.

In one example, the NO generation accelerant in the second solid formulation is selected from the group consisting of ascorbate sources, tocopherols and tocotrienols, those based on sulfur, thiol, or thiolate, those based on boron, silanes, those based on phosphine, hydride donors, metal based complexes, metal based agents, nitrogen based agents, and carbon based complexes. As such, any example of the NO generation additive disclosed herein for the first solid formulation may be included in the second solid formulation.

The second solid formulation also includes the pH buffer. The pH buffer is also in solid form, e.g., a powder, granular material, etc. and can be mixed with the other second solid formulation components. The pH buffer is present in the second solid formulation an amount sufficient to render a pH of the moisture or hydrating liquid activatable solid formulation from greater than 4 to about 9.0. In an example, the second solid formulation includes the pH buffer in an amount ranging from about 1 wt % to about 70 wt % based on the total weight of the second solid formulation.

The pH buffer renders and maintains the pH of the second solid formulation within the desired range of from greater than 4 to about 9.0. In some examples, the pH of the second solid formulation ranges from about 4.1 to about 8.5, e.g., from about 4.5 to about 8.0, or from about 4.5 to about 7.0, or from about 4.1 to about 6.9. While NO generation may be less form the solid formulation having a pH ranging from 8.0 to 9.0, the lower levels may be desirable in some applications.

The pH buffer may be a monobasic and/or dibasic phosphate, monocitric acid, dibasic citric acid, acetic acid, citrate, acetate, Tris-buffered saline (TBS), barbital buffer, collidine buffer, dimethylglutarate, succinate, maleate, malate, formate, propionate, imidazoles, pyridine, piperazine, histidine, ammonium chloride, ethylenediaminetetraacetic acid (EDTA), TRIS (tris(hydroxymethyl)aminomethane), BIS-TRIS (2-[Bis(2-hydroxyethyl)amino]-2-(hydroxymethyl)propane-1,3-diol), MOPSO (β-Hydroxy-4-morpholinepropanesulfonic acid), PIPES (1,4-Piperazinediethanesulfonic acid), BES buffered saline, MOPS (3-(N-Morpholino)propanesulfonic acid), TES (2-[[1,3-dihydroxy-2-(hydroxymethyl)propan-2-yl]amino]ethanesulfonic acid), HEPES (4-(2-Hydroxyethyl)piperazine-1-ethanesulfonic acid), DIPSO (3-(N,N-Bis[2-hydroxyethyl]amino)-2-hydroxypropanesulfonic acid), TRIZMA® (2-Amino-2-(hydroxymethyl)-1,3-propanediol), maleate, cacodylate, MES (4-morpholineethanesulfonic acid), ADA (N-(carbamoylmethyl)iminodiacetic acid), ACES (N-(carbamoylmethyl)taurine), Bis-Tris Propane (1,3-bis[tris(hydroxymethyl)methylamino]propane), MOBS (4-(N-morpholino)butanesulfonic acid), TAPSO (2-hydroxy-3-[tris(hydroxymethyl)methylamino]-1-propanesulfonic acid), HEPPSO (4-(2-hydroxyethyl)piperazine-1-(2-hydroxypropanesulfonic acid)), POPSO (Piperazine-N, N'-bis(2-hydroxypropanesulfonic acid), TEA (triethanolamine), EPPS (4-(2-hydroxyethyl)-1-piperazinepropanesulfonic acid), Tricine (N-[tris(hydroxymethyl) methyl]glycine), Glycine, Gly-Gly (diglycine), BICINE (N,N-bis(2-hydroxyethyl)glycine), HEPBS (N-(2-Hydroxyethyl)piperazine-N'-(4-butanesulfonic acid)), TAPS (N-[tris (hydroxymethyl)methyl]-3-aminopropanesulfonic acid), AMPD (2-amino-2-methyl-1,3-propanediol), TABS (N-tris (hydroxymethyl)methyl-4-aminobutanesulfonic acid), AMPSO (N-(1,1-dimethyl-2-hydroxyethyl)-3-amino-2-hydroxypropanesulfonic acid), POPSO (piperazine-N,N'-bis (2-hydroxypropanesulfonic acid, or CHES (N-cyclohexyl-2-aminoethanesulfonic acid).

For any of the pH buffers, it is believed that salt (e.g., counter ion variant, such as sodium, potassium, magnesium, calcium, etc.), hydration state (e.g., monohydrate, dihydrate, trihydrate, hemi(pentahydrate), hemihydrate, etc.), protonation state, or combinations thereof may be used.

The second solid formulation may also include one or more of the following: a binder, a lubricant, a hydration agent, an $NO_2$ scavenger, a desiccant, an oxygen scrubber, and combinations thereof. Any examples of the binder, the lubricant, the hydration agent, the $NO_2$ scavenger, and the desiccant may set forth herein for the first solid formulation may also be used in the second solid formulation. The respective amounts set forth herein for each of these components may be suitable for the second solid formulation.

An oxygen scavenger that is capable of removing oxygen (which is capable of reacting with NO to generate $NO_2$), and thus is capable of reducing the amount of $NO_2$ produced, may be used. Examples of a suitable oxygen scrubber include sodium metabisulfite, hydrazine, carbohydrazide, tannin, or diethylhydroxyamine (DEHA). The oxygen scrubber may be included in an amount of about 10 wt % or less, based on a total weight of the second solid formulation.

It is to be understood that the components of the second solid formulation (including the nitrite source) may be present in any suitable amounts. As such, the nitrite source, the copper catalyst, NO generation additive, the pH buffer, the binder, the lubricant, the hydration agent, the $NO_2$ scavenger, the desiccant and/or the oxygen scrubber may be present in any desired suitable amount. In some examples, the nitrite source is present in an amount ranging from about 1 wt % to about 80 wt %; the copper catalyst is present in an amount ranging from about 0.1 wt % to about 50 wt %; the NO generation additive is present in an amount ranging from about 1 wt % to about 70 wt %; the pH buffer is present in an amount ranging from about 1 wt % to about 70 wt %; the binder is present in an amount ranging from about 0.1 wt % to about 90 wt %; the lubricant is present in an amount ranging from greater than about 0.1 wt % to about 90 wt %; the hydration agent is present in an amount ranging from greater than about 0.1 wt % to about 50 wt %; the $NO_2$ scavenger is present in an amount ranging from greater than about 1 wt % to about 30 wt %; the desiccant is present in an amount ranging from about 0.1 wt % to about 30 wt %; and/or the oxygen scrubber is present in an amount ranging from greater than about 0.1 wt % to about 20 wt %. Each of these weight percentages is with respect to the total weight of the second solid formulation.

In some examples of the second formulation, the nitrite source is present in an amount ranging from about 4 wt % to about 20 wt %; the NO generation additive is present in an amount ranging from about 10 wt % to about 40 wt %; the copper catalyst is present in an amount ranging from about 1 wt % to about 22 wt %; the pH buffer is present in an amount ranging from about 1 wt % to about 25 wt %; the binder is present in an amount ranging from about 1 wt % to about 10 wt %; the lubricant is present in an amount ranging from greater than about 0.5 wt % to about 20%; the hydration agent is present in an amount ranging from greater than about 1 wt % to about 15 wt %; the desiccant is present in an amount ranging from about 2 wt % to about 12 wt %; and/or the oxygen scrubber is present in an amount ranging from about 0.5 wt % to about 10 wt %; and/or the $NO_2$ scavenger is present in an amount ranging from about 2 wt % to about 12 wt %.

The following are some specific examples of the second solid formulation:

i) sodium nitrite 9 wt %, calcium ascorbate 33 wt %, trisodium citrate 22 wt %, ascorbic acid 8 wt %, magnesium chloride 8 wt %, copper(II) bromide 7 wt %, and magnesium stearate 13 wt %;

ii) sodium nitrite 10 wt %, calcium ascorbate 37 wt %, trisodium citrate 26 wt %, ascorbic acid 9 wt %, magnesium chloride 9 wt %, copper(II) chloride 8 wt %, and magnesium stearate 1 wt %;

iii) potassium nitrite 10 wt %, sodium ascorbate 42 wt %, disodium phosphate 28 wt %, sodium chloride 9 wt %, copper(II) nitrate 5 wt %, and sodium stearate 6 wt %;

iv) sodium nitrite 25 wt %, sodium ascorbate 27 wt %, trisodium phosphate 16 wt %, ascorbic acid 10 wt %, calcium chloride 3 wt %, copper(II) sulfate 7 wt %, and ascorbyl palmitate 12 wt %;

v) sodium nitrite 14 wt %, sodium ascorbate 46 wt %, ascorbyl palmitate 10 wt %, monobasic sodium phosphate 24 wt %, silicon dioxide 4 wt %, and sodium stearate 1 wt %;

vi) potassium nitrite 16 wt %, sodium ascorbate 51 wt %, monobasic sodium phosphate 32 wt %, iron(II) chloride 1 wt %; and vii) sodium nitrite 15 wt %, calcium ascorbate 50 wt %, monobasic sodium phosphate 28 wt %, copper(II) acetate 5 wt %, and polyethylene glycol (PEG) 2 wt %.

In some examples, the second solid formulation may be maintained in sealed packaging until it is desirable to expose the formulation to moisture to generate NO. In other examples, the second solid formulation may be re-constituted in a hydrating liquid, such as deionized or purified water, to generate one example of the liquid form of the NO generating formulation.

The examples of the first and second solid formulations may be part of an NO generation kit. Examples of the kit include the solid formulation (e.g., powder, pellet, etc.) and a reconstitution solution. The solid formulation and reconstitution solution may be maintained separately until it is desirable to generate NO. When combined, the solid formulation and reconstitution solution are mixed to form the liquid form of the NO generating formulation NO. In one example, the solid formulation includes the NO adduct/donor (and in some instances the hydrophilic binder) and the reconstitution solution includes the hydrating liquid and the NO generation additive. In another example, the solid formulation includes the nitrite source, the copper catalyst, the NO generation additive, and the pH buffer (alone or in combination with one or more of the binder, the lubricant, the hydration agent, the oxygen scrubber, the $NO_2$ scavenger, and the desiccant) and the reconstitution solution includes the hydrating liquid.

In any of the NO formulation examples, the solid formulations (e.g., pellet/tablet/disk, powder etc.) or the re-constituted liquid (e.g., pellet, tablet or powder in a hydrating liquid) may be used in an NO generating system for a predetermined amount of time (e.g., the user may be notified that "x" ppm of NO will be generated for "y" hours), after which the user may be directed to replace the solid formulation or to introduce a fresh re-constituted liquid. In a further example, an NO detector may be used to indicate when the NO generating formulation no longer generates a desired amount of NO. In yet a further example, the solid may be formulated to dissolve when the NO generating formulation no longer generates a desired amount of NO.

Containers

Several different containers are contemplated herein. Some examples of the container function as outer packaging, which protects the NO generating formulation from premature water vapor and/or light exposure and/or from premature hydration, and which can be removed prior to use. Other examples of the container function to contain the NO generating formulation during use (and thus may be NO permeable). In some of the examples disclosed herein, a container having the NO generating formulation therein is held within an outer package container prior to use. Several different containers will now be described.

Any example of the NO generating formulation disclosed herein may be contained in an outer package, such as a foil or plastic pouch (e.g., biaxially-oriented polyethylene terephthalate, such as commercially available MYLAR®). This type of outer package serves to hermetically seal the NO generating materials from humidity and light that can affect the effectiveness and time release characteristics of the NO generating formulation, as well as its useful life. In some examples, the outer package hermetically seals the solid form of the NO generating formulation (e.g., the first solid formulation or the second solid formulation). In these examples, a user would remove the solid NO generating formulation, in the form of a pellet, disk, tablet, or powder from the outer package prior to use. In some examples, the outer package hermetically seals a pouch or other holder (e.g., a sachet) containing the NO generating formulation. In these examples, a user would remove the NO permeable pouch or holder from the outer package prior to use. In some examples, the outer package hermetically seals a powder of the NO generating formulation. In these examples, when the outer package is opened, the powder is ready for hydration or moisture exposure, possibly inside the outer package itself. In still another example, the outer package may be a single container that has two (2) chambers, one for the NO generating formulation and the second for a hydrating liquid. The components of the two chambers can be mechanically forced to blend together. Such a container could also have holes or a membrane for the NO to escape after mixing. In still another example, the outer package hermetically seals an absorbent pad that is coated with or includes the first or second solid NO generating formulations. In these examples, the absorbent pad is removed from the hermetically sealed outer container for humidity and/or liquid activation. Still another approach would be to supply the NO generating formulation in a premixed ampule that can be opened and poured into a device, such as the one depicted in FIG. 26.

Other examples of the container function to contain the NO generating formulation during use (and thus may be NO permeable). An example of a suitable container is a pouch.

The NO permeable container may be a woven or a non-woven material (e.g., cloth, fabric, etc.). In some examples, the NO permeable container is a hard shell made of plastic, metal, or another material that does not interfere with NO generation and that does not absorb/adsorb the generated NO. In one example, the NO permeable container is selected from the group consisting of a woven material, a non-woven material, a plastic material, and a metal material.

The NO permeable container may also be porous. The pores may be nanopores (e.g., having a diameter ranging from about 1 nm to less than 1000 nm) or micropores (e.g., having a diameter ranging from about 1 μm to less than 1000 μm).

When the NO generating formulation is sensitive to water vapor, the container may be permeable to humidified air and to NO. This type of container enables the humidified air to enter into contact with the nitric oxide generating formulation (e.g., the first or second solid formulations), and also enables generated gaseous NO to be released from the container. Examples of suitable materials for the air and NO permeable container include polyethylene, polyamide, polytetrafluoroethylene (PTFE), polypropylene, polyvinylidene difluoride, etc.

When the NO generating formulation is light sensitive, the container may be transparent to blue and/or UV light and permeable to NO. An example of an NO permeable and light transparent material for the container includes polycarbonate, such as polycarbonate track etch membranes. Commercially available NO permeable and light transparent membranes include WHATMAN® NUCLEPORE™ Track-Etched Membranes (from GE Healthcare) and TRAKETCH® (from Sabeu). These membranes may be nanoporous (e.g., diameter ranging from about 1 nm to less than 1000 nm) or microporous (e.g., diameter ranging from about 1 μm to less than 1000 μm).

Figure 22:
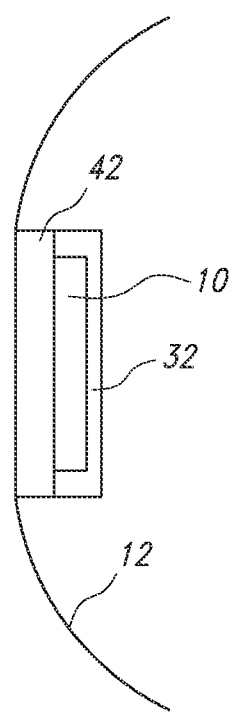
FIG. 22 is a schematic illustration of the NO generating system of FIG. 21 affixed to an inhalation device.
Figure 23:
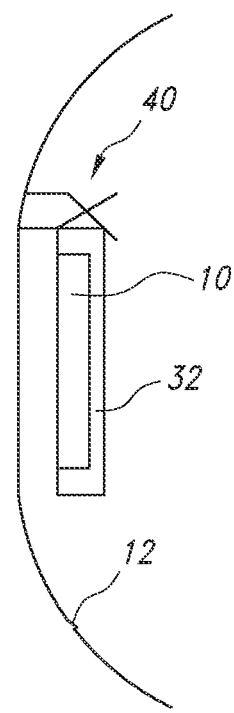
FIG. 23 is a schematic illustration of another example of an NO generating system affixed to an inhalation device.

Some examples of the NO permeable container include an attachment mechanism. The attachment mechanism may be used to secure the NO permeable container (and the NO generating formulation therein) to the inside or the outside of an inhalation device or another housing. Some examples of the attachment mechanisms are shown in FIGS. 21 through 23.

Figure 21:
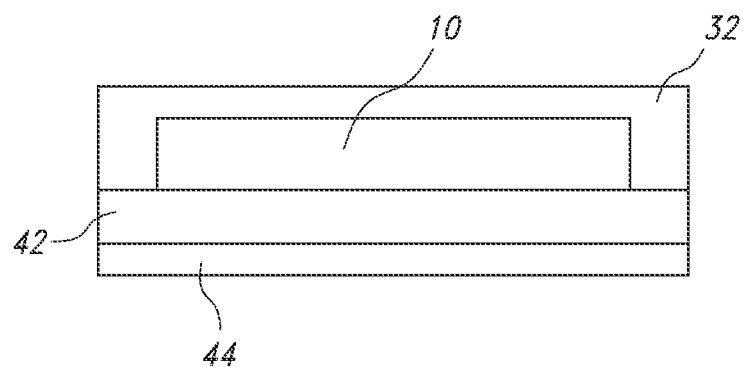
FIG. 21 is a schematic illustration of an example of an NO generating system including a container, an adhesive that may be formed into a disk, tablet or other shape, and a peal-away liner.

In FIG. 21, the container 32 is a pouch and the attachment mechanism includes an adhesive 42 covered by a peal-away adhesive liner 44. The adhesive 42 is positioned on one surface of the container 32, and the peal-away adhesive liner 44 covers the adhesive 42 until it is removed by a user. An example of an adhesive is a pressure-sensitive adhesive or a double sided adhesive. When the peal-away adhesive liner 44 is removed, the adhesive 42 can secure the container 32 to the inside of an inhalation device, such as a face mask 12, as shown in FIG. 22.

Another example of the attachment mechanism is a clip. A clip 46 is schematically shown in FIG. 23. One portion of the clip 46 is attached to the container 32 (e.g., pouch), and another portion of the clip 46 is attached to the inhalation device, such as a face mask 12. While a clip 46 has been illustrated, it is to be understood that other example mechanical attachment mechanisms may be used instead of a clip, examples of which include hooks, clamps, pins, or the like.

The container 32 may be prepared using any suitable method, including molding processes, 3D printing processes, etc.

Some examples of the container 32 further include a filter on a surface of the container 32 or positioned outside of the container 32, the filter including absorbent to scavenge nitrogen dioxide ($NO_2$) released by the NO generating formulation, a reagent to convert generated $NO_2$ back to NO, or combinations thereof. In some examples, the filter is a nitrogen dioxide ($NO_2$) filter. The $NO_2$ filter may be positioned to receive the output gas NO before it is inhaled by the patient. In some examples, the $NO_2$ filter may be positioned on an outside of the container 32 on a surface that is to face a user's mouth and/or nose. Some examples of the $NO_2$ filter remove at least some of the nitrogen dioxide from the NO gas. As examples, a silica gel filter (with preconditioned silica particles) or a soda lime scrubber may be used as the NO filter. These filters may reduce the $NO_2$ to a level that is not physiologically relevant. Other examples of the $NO_2$ filter convert the nitrogen dioxide back into nitric oxide. This conversion is desirable because no NO payload is lost in the form of scavenged (absorbed) $NO_2$, but rather is reduced back into NO. An example of this type of $NO_2$ filter includes ascorbic acid impregnated silica particles.

Inhalation Devices

In some examples, the nitric oxide (NO) generating system further includes an inhalation device in operative contact with the NO generating formulation. Examples of inhalation devices include face masks, nasal cannulas, nose pillows (also referred to herein as "nose vent plugs"), and ventilators.

In an example of the NO generating system, the inhalation device comprises a face mask 12. FIGS. 2-7 show various examples of suitable face mask configurations. FIGS. 22-24 also show various examples of suitable face mask configurations. The examples shown in FIGS. 22-24 also include different examples of the container 32. In some of the face mask 12 examples, the first solid formulation or the second solid formulation (e.g., NO generating formulation 10, 10')

is manufactured separately and then introduced into the face mask 12. In other of the face mask examples, the first solid formulation or the second solid formulation may be manufactured as part of the face mask.

Face masks 12 (also known as filtration respirators) may be used to protect the respiratory system from particulate or chemical agents. Face masks 12 may be designed to minimize the transmission of contagious diseases or to protect the respiratory system from toxic substances or allergens in the surrounding atmosphere. In addition, face masks 12 may be used to protect from inhalation of industrial or city dust or dirt, chemicals, allergens, etc. that may be present in the atmosphere. Face masks 12 may be used to maintain an enclosed space around the breathing orifices when a person is in close proximity to other persons, or if an undesirable atmospheric agent is present. Additionally, infectious persons may wear face masks 12 to protect other people in the vicinity from their pathogens. It is to be understood that while the face masks disclosed herein are described in context of a person, adaptations for anatomical features of any breathing organism are contemplated and disclosed herein. For example, face masks may be adapted for dogs, cats and horses.

In an example, the first solid formulation or the second solid formulation (e.g., in the form of a solid disk, pellet, powder in a pouch/sachet, etc.) may be placed within the face mask 12 without being secured or affixed thereto. In this example, the first solid formulation or the second solid formulation or the container holding the formulation is left loose in the face mask 12. In some examples, the first solid formulation or the second solid formulation is contained within the NO permeable container 32, and the NO permeable container 32 is to be disposed in the face mask 12 without being affixed, or otherwise secured, thereto.

In another example, the face mask 12 includes a housing 14 (in FIGS. 2A-2C and 3A-3C) to hold the first solid formulation or the second solid formulation in effective proximity to at least one of a mouth or a nose of a user. FIGS. 2C and 3C illustrate the face mask 12 in position on the user's face, and also illustrate the first solid formulation or the second solid formulation (shown as NO generating formulation 10, 10') in effective proximity to at least one of a mouth or a nose of a user.

Figure 2C:
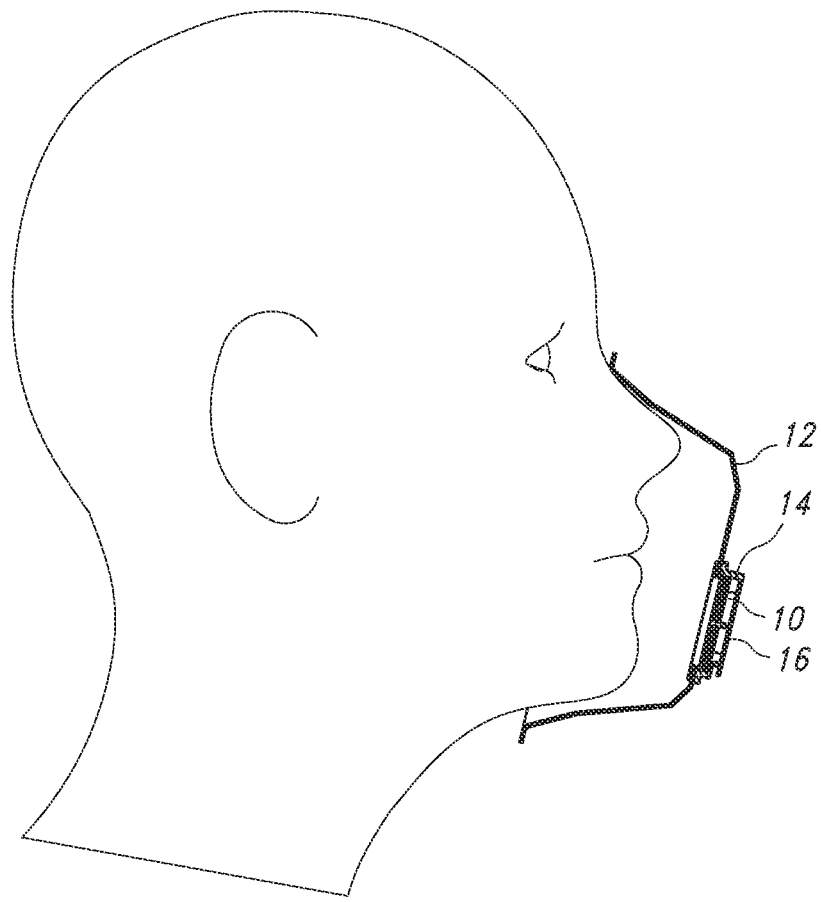
FIG. 2C is a side view of the face mask inhalation device of FIG. 2B, showing the NO generating formulation in place proximate to the area where a user's nose and mouth would be.
Figure 3A:
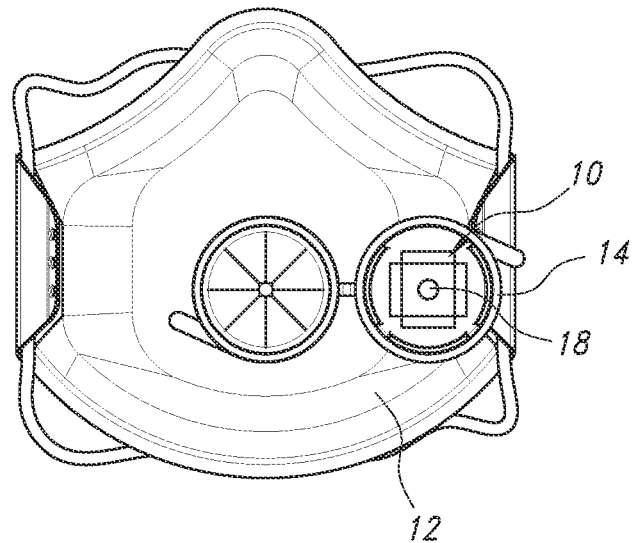
FIGS. 3A and 3B are schematic illustrations of another example face mask inhalation device, showing the NO generating formulation-holding housing in an opened position (FIG. 3A) and a closed position (FIG. 3B)
Figure 3B:
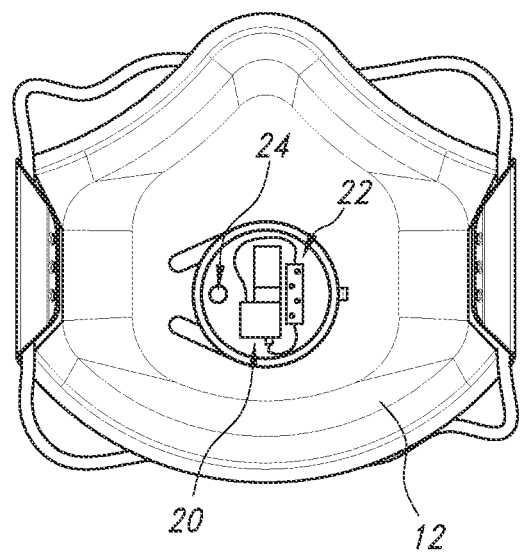
Figure 3C:
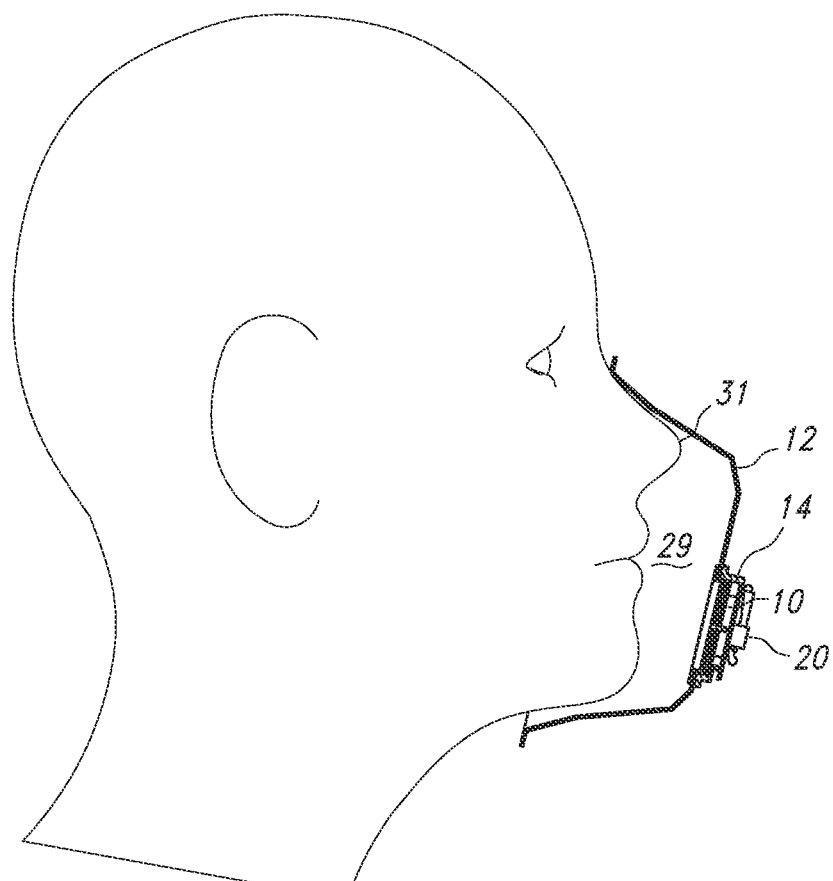
FIG. 3C is a side view of the face mask inhalation device of FIG. 3B, showing the NO generating formulation in place proximate to the area where a user's nose and mouth would be.

In the examples shown in FIGS. 2A-2C and 3A-3C, the housing 14 selectively opens and closes. FIGS. 2A and 3A depict a door of the housing 14 in an open position (e.g., which is used to introduce the first solid formulation or the second solid formulation, e.g., NO generating formulation 10, 10', into the face mask 12), and FIGS. 2B and 3B depict the door of the housing 14 in a closed position (e.g., which is used when it is desirable to introduce NO gas to the user).

The open configuration shown in FIG. 2A and FIG. 3A depicts four (4) of the single solid pellets/tablets installed in a door of the housing 14. Each individual single solid pellets/tablets is an example of the NO generating formulation 10, 10' (which may be the first solid formulation or the second solid formulation disclosed herein). In the example shown, the NO generating formulation 10, 10' includes a single solid. It is to be understood that any number of single pellets/tablets that will generate a desirable level of NO gas at a given time may be used as the NO generating formulation 10, 10'. As such, when multiple single solid pellets/tablets are used together, the plurality of the single solids may collectively be referred to as the NO generating formulation 10, 10'. In some examples then, the NO generating formulation 10, 10' includes a plurality of the single solids.

In the examples shown in FIGS. 2A and 3A, each single pellets/tablets (e.g., NO generating formulation 10, 10' made up of the first solid formulation or the second solid formulation) may be snapped in place in the door of the housing 14. In other examples, each single pellets/tablets (e.g., NO generating formulation 10, 10') may be slid into a respective receptacle defined in the door of the housing 14. Other suitable mechanisms may also be used to hold the single solid form of the NO generating formulation 10, 10' in the housing 14.

Although the door is shown as able to rotate open about a living hinge, it is to be understood that the housing door may be configured/designed in such a manner that it may be selectively opened and closed by any suitable type of motion, e.g., rotating, sliding, flipping, etc. It is to be understood that the housing 14 shown in FIGS. 2A-2C and FIGS. 3A-3C is an example, but that any suitable attachment structure or device may be used as the housing 14. For example, the housing of the face mask 12 may include a flap or pouch (on the interior or exterior) that can receive and hold the first solid formulation or the second solid formulation (e.g., NO generating formulation 10, 10').

In the example of the face mask inhalation device (face mask 12) shown in FIG. 3A, the housing 14 further includes an air humidifier 22 in operative contact with the first solid formulation or the second solid formulation (e.g., NO generating formulation 10, 10', shown as tablets/pellets); an air pump 20 in fluid communication with the air humidifier 22; and a source of electrical power (shown as a battery 24 in the figure) operatively connected to the air humidifier 22 and to the air pump 20. As shown in FIG. 3A, the housing 14 has an air inlet 18 defined therethrough. The air pump 20 may be connected to the air inlet to transport any water vapor generated by the air humidifier 22 through the air inlet 18 and thus within proximity of the NO generating formulation 10, 10'. It is to be understood that "fluid communication" is to be interpreted broadly to include, e.g., liquids and gases.

As shown in FIG. 3B, the air humidifier 22 and air pump 20 are small enough to fit on or in the housing 14. The battery 24 power may be sufficient to operate both the air humidifier 22 and air pump 20, or separate batteries 24 may be operatively connected to the air humidifier 22 and air pump 20. The air humidifier 22 may be used in any of the examples disclosed herein to generate moisture (e.g., water vapor), with or without moisture that may come from the user's exhalation. The air pump 20 may be used to transport the generated water vapor within proximity of the NO generating formulation 10, 10', and may also transport generated NO gas to the user.

Figure 8:
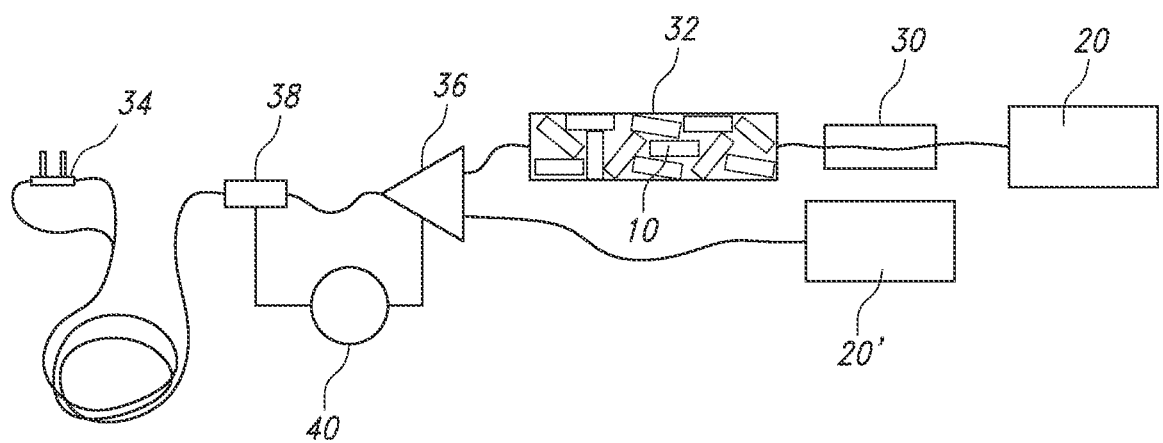
FIG. 8 is a schematic illustration of an example inhalation system inhalation device including a nasal cannula.

A further example of the face mask inhalation device is not shown, but is similar to the example system shown in FIG. 8. In this example, the face mask inhalation device includes: an air pump 20 operatively connected to the face mask 12; an air humidifier 22 in fluid communication with the air pump 20; and a container 32 to hold the NO generating formulation 10, 10' (the first solid formulation or the second solid formulation), the container 32 in fluid communication with the air humidifier 22 and with the face mask 12. In yet a further example, the face mask inhalation device further includes: a gas mixer in fluid communication with the container; a second air pump operatively connected to the gas mixer; an NO sensor operatively connected between the gas mixer and the face mask; and a feedback controller operatively connected to the NO sensor and to the gas mixer. This example is similar to the system shown in FIG. 8, except that the nasal cannula 34 (in FIG. 8) is replaced with a face mask 12. In this example, the face mask 12 may not have a housing 14, but may have an adapter to attach a conduit (e.g., tube) that is also in fluid communication with the container 32.

In still other examples, the housing 14 of the face mask 12 may be configured to receive and contain a liquid that generates the NO gas. In some examples, the housing 14 at least partially defines a reservoir that is to receive a predetermined volume of a hydrating liquid having the NO generating formulation 10, 10' (or other form of the first solid formulation or the second solid formulation) dissolved (or dispersed) therein. In these examples, the first solid formulation or the second solid formulation may be mixed with a prescribed/predetermined volume of water, and then the re-constituted solution may be poured into the housing 14. In other examples, the solid formulation may be contained in a sachet in the housing 14, and then the hydrating liquid may be poured or introduced into the housing 14. In still other examples, the housing 14 may contain an absorbent that is coated with the NO generating formulation or can hold a liquid form of the NO generating formulation.

Figure 26:
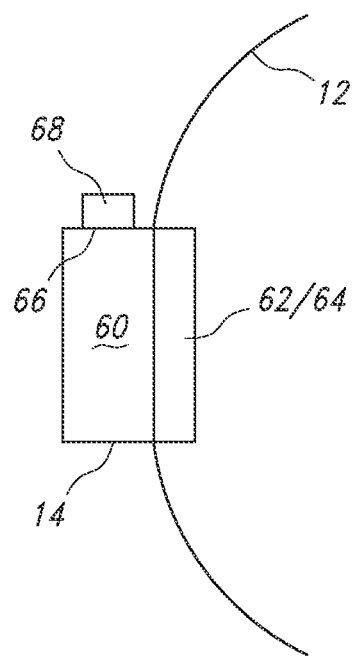
FIG. 26 is a schematic illustration of yet another example of an NO generating system affixed to an inhalation device.

One of these examples is shown in FIG. 26. In this example, the housing 14 partially defines a reservoir 60 and includes a reservoir wall 62 or filter 64 positioned between the interior of the face mask 12 and the interior of the reservoir 60. The reservoir wall 62 or filter 64 may be made of a non-porous, NO permeable material, such as polyurethane, poly(tetrafluoroethylene), etc. A reservoir wall 62 or filter 64 made of this type of material will allow the NO gas to permeate therethrough (e.g., into the face mask 12), but will also be resistant to leakage of the hydrating liquid containing the dissolved or dispersed first or second solid formulation. In other words, the reservoir wall 62 or the filter 64 is impermeable to a hydrating liquid and is NO permeable. As such, the reservoir wall 62 or filter 64 enables NO gas generated within the reservoir 60 to be inhaled by the user without allowing the liquid to escape. When the filter 64 is positioned between the interior of the face mask 12 and the interior of the reservoir 60, the filter 64 may include an absorbent to scavenge nitrogen dioxide ($NO_2$) released by the NO generating formulation, a reagent to convert generated $NO_2$ back to NO, or combinations thereof.

In these examples, the housing 14 may not be movable between open and closed positions (e.g., as shown in FIGS. 2A and 2B), but may include a sealable input port 66 where the liquid can be introduced into the reservoir 60. A removable cap 68 can be used to seal the sealable input port 66.

While not shown in FIG. 26, this example may further include an absorbent material in the reservoir 60. The absorbent material will absorb the liquid (e.g., the hydrating liquid), but will allow the NO gas to permeate out of the material and through the reservoir wall 62 or filter 64. Examples of the absorbent material that can be included in the reservoir 60 include a cotton ball or a compressed cotton or similar material that will not affect the production of NO. In these examples, the sealable input port 66 may be configured as a larger opening or door for introduction of the absorbent pad and an example of the liquid form of the NO generating formulation, or for introduction of the absorbent pad containing the first or second solid NO generating formulation and an activating liquid (e.g., water).

The reservoir 60 in FIG. 26 can also receive the container 32 containing the solid NO generating formulation 10, 10' therein.

Another configuration not shown in FIG. 26 is the use of a fan to blow the NO generated by the NO generating formulation out of the reservoir and toward a user of the inhalation device.

Also while not shown in FIG. 26, it is to be understood that this example of the device may include an additional filter that contains a reagent or catalyst to convert any $NO_2$ into NO. This filter may be positioned between the reservoir wall 62 or filter 64 and the interior of the face mask 12 to keep $NO_2$ from reaching the user.

The example shown in FIG. 26 may also include a diverter valve (not shown) that would channel exhaled breath out of the device (e.g., face mask 12) without interacting with the reservoir 60 containing the NO generating formulation. The design of this valve would allow the inhaled breath to move past the NO generating formulation (e.g., the first or second solid formulations) and into the user's mouth and/or nose.

The example shown in FIG. 26 may also include a chamber (fluidly connected to the reservoir 60) where the outgassing NO could build up during respiration pauses and during the period of exhalation through a diverter valve. The stored NO may then be available as a pulsed concentration during inhalation.

In any of the example face masks 12 that can receive the re-constituted solution or dispersion (e.g., hydrating liquid with the first or second solid formulation therein), it is to be understood that the housing 14 (and thus the reservoir 60) may be integrally formed with the face mask 12, or may be a separate housing 14 attached to the face mask 12.

Figures 4A, 4B:
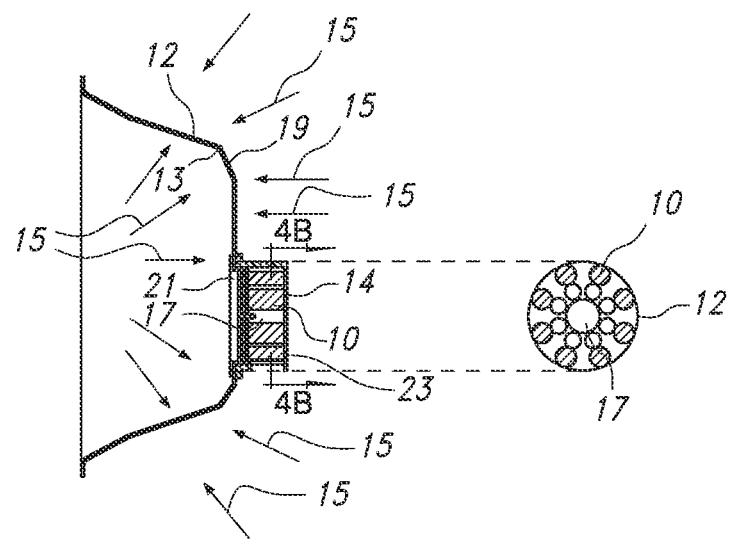
FIG. 4A is a schematic illustration showing a side view of another example face mask inhalation device.
FIG. 4B is a cross-sectional view taken through line 4B-4B of FIG. 4A, depicting multiple pellets of the NO generating formulation in the housing.

The examples depicted in FIG. 4A-FIG. 7 illustrate some additional configurations for implementing the first or second solid formulations (e.g., NO generating formulation 10, 10') into the face mask 12. FIGS. 4A and 4B illustrate another example of how a plurality of the single pellets/tablets of the NO generating formulation 10 may be arranged in the housing 14. In this example, the housing 14 may include individual receptacles for the single pellets/tablets of the NO generating formulation 10. Alternatively, the single pellets/tablets of the NO generating formulation 10 may be secured to a cap ring that can be loaded into the housing 14.

Figure 5:
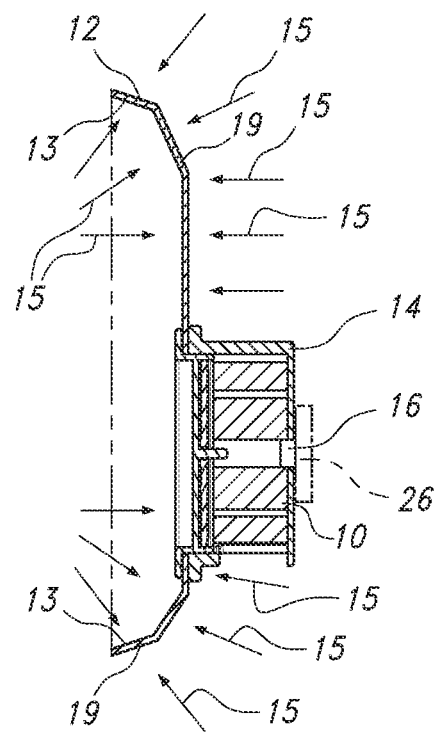
FIG. 5 is a schematic illustration showing a side view and end view of the example face mask inhalation device of FIG. 2.
Figure 6:
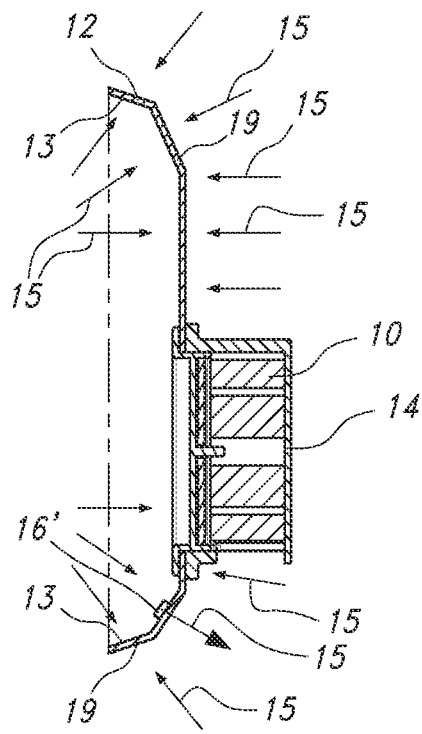
FIG. 6 is a schematic illustration showing a side view of yet another example face mask inhalation device.
Figure 7:
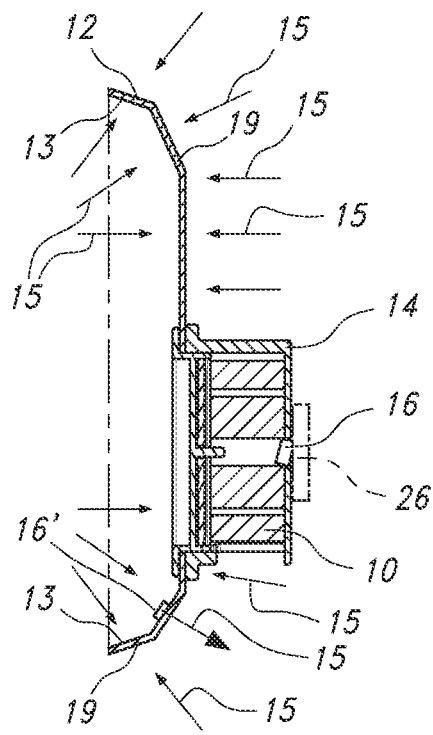
FIG. 7 is a schematic illustration showing a side view of still another example face mask inhalation device.

The configurations in FIGS. 5-7 also include check valves, such as inhalation check valves 16 (FIGS. 2A-2C and FIG. 5), exhalation check valves 16' (FIG. 6), or both inhalation check valves 16 and exhalation check valves 16' (FIG. 7)). The check valve(s) 16, 16' may help to prevent exhaled air from going back into the NO generating formulation 10, 10', as this could undesirably expel NO gas from the system.

The examples shown in FIGS. 5 and 7 also illustrates a filter 26 positioned on the outside of the face mask 12 adjacent to the one-way in check valve 16. This filter 26 may be an N95 or an N99 filter.

In examples, the face mask 12 includes a filtering face mask. As used herein, a filtering face mask means a mask that covers at least the nose and the mouth of a wearer and that includes a filter element 19 to remove contaminants and/or particles from air that passes through the filter element 19. As shown in FIG. 4A, the mask body 13 is a filter element 19 that is molded to fit contours of the face of the wearer. As depicted by airflow direction arrows 15, the filter element 19 is a bi-directional filter that is to filter air during inhalation and exhalation. As depicted in FIG. 4A, the housing 14 is mounted through the mask body 13 and attached thereto. As depicted in FIG. 4A and FIG. 4B, the NO generating formulation 10 is distributed around an aperture 17 defined in an interior wall 21 of the housing 14. In the example shown in FIG. 4A, an exterior wall 23 of the housing 14 may be composed of the non-porous, NO permeable material described above. In another example, the exterior wall 23 of the housing 14 may be composed of a non-porous, NO impermeable material. As shown in FIG. 5, an inhalation check valve 16 is to open to allow air to pass through the exterior wall 23 of the housing 14 in an inhalation direction. The inhalation check valve 16 is to close to block air from passing through the exterior wall 23 of the housing 14 in an exhalation direction opposite to the inhalation direction. As depicted in FIG. 5, a filter 26 may be connected to the housing 14 to filter the air before the air passes through the inhalation check valve 16. This filter 26 may have any desirable filtration characteristics, for example the filter 26 may be an N95 filter or an N99 filter. It is recognized that filter 26 operates in parallel with the filter element 19. Thus, the flow characteristics of the filter 26 and filter element 19 are interdependent. For example, if it is too easy to draw air through the filter element 19 compared to the filter 26, most of the air will take the path of least resistance through filter element 19.

The example depicted in FIG. 6 is similar to the example depicted in FIG. 4B with an exhalation check valve 16' installed on the mask body 13. In an open position, the exhalation check valve 16' is to allow air to pass through the mask body 13 in an exhalation direction 27. In a closed position, the exhalation check valve 16' is to block air from passing through the check valve 16' in an inhalation direction opposite to the exhalation direction 27. Thus, an exhalation check valve 16' may allow at least a portion of exhaled air to bypass the filter element 19, to, for example, reduce humidity that may otherwise accumulate in an interior space 29 bounded by the face mask 12 and the face 31 (See, e.g., FIG. 3C) of the wearer. As depicted in FIG. 7, examples of the present disclosure may include a combination of an inhalation check valve 16 with a filter 26 as shown in FIG. 5 and an exhalation check valve 16' as shown in FIG. 6.

Referring now to FIG. 8, another example of the inhalation device comprises an inhalation system, including: an air pump 20; an air humidifier 30 (hydrator) in fluid communication with the air pump 22; a container 32 (such as, for example, a canister) to hold the first or second solid formulations (shown as several RSNO pellets/tablets, e.g., 10 or 10', within a canister), the container 32 in fluid communication with the air humidifier 30; and a nasal cannula 34 (or a ventilator (not shown)) in fluid communication with the container 32. This example includes the configuration shown at the top of FIG. 8, but without the gas mixer 36 or NO sensor 38. However, it is to be understood that an NO sensor 38 may be used if desired in this configuration.

In another example, the inhalation system further includes: a gas mixer 36 in fluid communication with the container 32; a second air pump 20' (shown at the bottom of FIG. 8) operatively connected to the gas mixer 36; an NO sensor operatively connected between the gas mixer 36 and the nasal cannula 34 (or the ventilator); and a feedback controller 40 operatively connected to the NO sensor 38 and to the gas mixer 36.

The second air pump 20' introduces an oxygen-containing gas to the gas mixer, where the oxygen-containing gas is mixed with the NO gas to form an output gas that is transported to the inhalation device (e.g., nasal cannula 34, or in other examples, the face mask 12 or ventilator). The oxygen-containing gas may be at least substantially pure oxygen gas $O_2$, or air, or a hypoxic gas that includes oxygen. While an air pump 20' is shown in FIG. 8, the oxygen-containing gas may be delivered from any suitable gas source (e.g., a compressed gas cylinder (not shown)), which can regulate the flow of the oxygen-containing gas, or can be coupled to a flow controller to regulate the flow of the oxygen-containing gas into the gas mixer. Any suitable gas flow rate may be used. As an example, the flow rate of the oxygen-containing gas may range from about 50 mL/min to about 5 L/min. In another example, the flow of the oxygen-containing gas may be regulated so that the output gas stream contains from about 20% oxygen to about 99.99% oxygen. In an example, 100% air saturation may be used as the oxygen-containing gas, which corresponds to about 10 mg/L (ppm) of $O_2$ in the output gas stream.

It is to be understood that the NO sensor 38 may be used to monitor the NO levels in the output gas stream from the container 32 (or from the gas mixer 36 if present in the system). It may be desirable to monitor the NO level in order to avoid forming $NO_2$ (nitrogen dioxide, which can be generating from $O_2$ reacting with NO and can be undesirable for a recipient/patient). Any suitable NO sensor 38 may be used.

In an example, the NO sensor 38 is a Shibuki-style sensor (not shown), which is based on the oxidation of NO to nitrate ($NO_3$) at an inner platinum (Pt) electrode position behind a gas permeable membrane.

Another example of an NO sensor 38 is an amperometric NO sensor which exhibits relatively rapid response times, and the high surface area of the working electrode(s) yields larger currents than the Shibuki configuration.

Some examples also include an $NO_2$ sensor, which may be used to monitor the $NO_2$ levels in the output gas stream from the container 32 (or from the gas mixer 36 if present in the system).

The NO sensor data (i.e., the concentration of NO in the output gas stream and/or the concentration of $NO_2$ in the output gas stream) may be used, e.g., by a feedback controller 40, to regulate the system to achieve an at least substantially constant concentration of NO at the delivery end. The data may also be used to regulate the flow of the output gas stream.

A target level of NO may be based upon the given application in which the NO is being used. The target level may be very low or very high, depending upon the patient and the application. As examples, the target level of NO for a newborn on inhalation therapy may range from about 10 ppm to about 70 ppm, and the target level of NO to be generated to prevent activation of platelets and other cells during bypass surgery may range from about 190 ppm to about 210 ppm. Further, for antimicrobial applications, such as for lung infections, lower levels of NO may be useful for inhalation therapy, in the range of, for example, from about 500 ppb to about 10 ppm.

As mentioned above, the sensor data may also be used to determine whether an undesirable amount of $NO_2$ is present in the output gas stream. If an undesirable amount of $NO_2$ is present, an alarm on the system may be activated. Moreover, a soda lime scrubber or other $NO_2$ scavenger may be included in the inhalation device, just before the output gas stream is delivered to the patient via, e.g., the nasal cannula 34, face mask 12, nose vent plug (see FIGS. 25A-25C), or ventilator (not shown). If the $NO_2$ content is greater than 1 ppm-3 ppm in the final gas phase, the soda lime scrubber can remove the excess $NO_2$.

In other examples similar to FIG. 8, the air humidifier 22 may be replaced with a reservoir of a hydrating liquid (e.g., water). The reservoir may be configured to introduce a prescribed/predetermined volume of the hydrating liquid into the container 32, and thus in contact with the NO generating formulation 10, 10' contained therein. Within the container 32, the hydrating liquid will activate NO gas generation. In some examples, the NO generating formulation 10, 10' is designed to release a prescribed volume of NO gas when it is mixed with the prescribed volume of the hydrating liquid. The NO gas can then be transported to the gas mixer 36, where it is mixed with the oxygen-containing gas, and delivered to a patient. In these examples, the reservoir may be refillable, so that fresh hydrating liquid may be introduced. Additionally, the container 32 may be refillable, so that the spent liquid can be removed, and fresh solid pellets/tablets of the NO generating formulation 10, 10' may be introduced after a cycle of NO gas generation has been performed.

In still other examples similar to FIG. 8, the air humidifier 22 may be replaced with a reservoir of the hydrating liquid. The reservoir may be configured to introduce a prescribed/predetermined volume of the hydrating liquid into the container 32, and thus in contact with the first or second solid formulation contained therein. Within the container 32, the hydrating liquid will activate NO gas generation. In some examples, the NO adduct/donor or nitrite source is designed to release a prescribed volume of NO gas, e.g., ranging from about 1 ppm to about 250 ppm. The NO gas can then be transported to the gas mixer 36, where it is mixed with the oxygen-containing gas, and delivered to a patient. In these examples, the reservoir may be refillable, so that fresh hydrating liquid may be introduced. Additionally, the container 32 may be refillable, so that the spent liquid can be removed, and fresh first or second solid formulation may be introduced after a cycle of NO gas generation has been performed.

Although a face mask 12 and a nasal cannula 34 have been shown as examples of the inhalation device, it is to be understood that a ventilator, or any other suitable apparatus for delivering the output gas stream to the airways of a user/patient may be used in accordance with examples of the present disclosure.

In some examples, the first or second solid formulation is contained within an example of the container 32, and the container 32 is introduced to the inhalation device. In some examples, the container 32 may simply be placed within the inhalation device. In other examples, such as those shown in FIGS. 21 and 22, the NO permeable container 32 is affixed to the inhalation device via the attachment mechanism. In each of these examples, the inhalation device is a face mask 12.

In the example shown in FIG. 22, an interior surface of the face mask 12 comes into contact with the adhesive 42 (after the liner 44 is removed) and holds the container 32 inside the face mask 12. The container 32, and thus the first or second solid NO generating formulation (which in this example is moisture activated), is held in effective proximity to at least one of a mouth or a nose of a user.

In the example shown in FIG. 23, the interior surface of the face mask 12 includes a receiving portion that can secure the clip 46, and thus the container 32, to the face mask 12. Via the clip 46, the container 32, and thus the NO generating formulation 10, 10' (which in this example is moisture activated), is held in effective proximity to at least one of a mouth or a nose of a user.

In the examples shown in FIGS. 22 and 23, the user's breath delivers sufficient humidity to release the gaseous NO that is drawn into the nose and mouth upon normal respiration. However, these examples can also include an air humidifier 22 and an air pump 20.

In other examples, the stable NO donor/adduct (of some examples of the first solid formulation disclosed herein) is blue or ultraviolet (UV) light activatable, and the NO generating system further comprises a blue or UV light source 50 positioned to illuminate the NO generating formulation 10, 10'. In some examples, the NO generating formulation 10, 10' and the blue or UV light source 50 are positioned on or in the inhalation device in a manner that will effectively illuminate the NO generating formulation 10, 10' to generate nitric oxide.

Figure 24A:
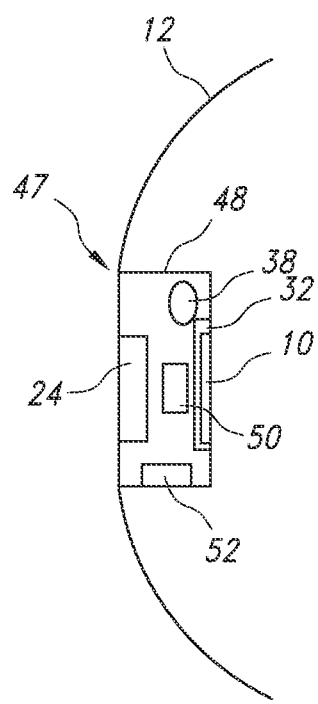
FIG. 24A is a schematic illustration of an example of a light activated NO generating system affixed to an inhalation device.

FIG. 24A depicts one example of a light activated NO generating system 47 inside of the inhalation device (e.g., face mask 2). In some examples, the light activated NO generating system 47 includes the NO generating formulation 10, 10' (the light activated first solid formulation) contained within a pouch (or other container 32) that is both NO permeable and blue and/or UV light transparent. In other examples, the NO generating formulation 10, 10' may be chemically or physically adhered to an interior wall of a housing 48 (without the container 32).

The example of the system 47 shown in FIG. 24A also includes a housing 48 in which the NO permeable container 32 is attached; a blue or UV light source 50 positioned within the housing 48 to illuminate the NO container 32; and a battery 24 operatively connected to the blue or UV light source 50.

The housing 48 of the light activated NO generating system 47 may be any material that can hold the various components and that also allows the generated NO gas molecules to release into the interior of the face mask 12 for inhalation by a user/patient. While the example shown in FIG. 24A includes a housing 48 for the NO permeable container (which contains the light activated first solid NO generating formulation 10, 10'), it is to be understood that the NO generating formulation 10, 10' may alternatively be coated as a film on a surface of the inhalation device. In these examples, the coating/film of the NO generating formulation 10, 10' would be applied to an interior surface of the inhalation device and the blue or UV light source 50 would be positioned within the inhalation device to illuminate the coating/film.

Any blue or UV light source 50 may be used that is capable of emitting light that initiates photolysis of the solid, light sensitive NO donor/adduct may be used. In other words, any light source 50 may be used that is capable of emitting the particular wavelength or wavelengths of light that cause the nitric oxide to be released from the NO donor/adduct. As such, the light source 50 may depend, in part, upon the NO donor used and the desired rate of NO release. As examples, the light source 50 may be a high intensity light emitting diode (LED), a laser diode, a lamp, etc. In one example, the blue or UV light source is a light emitting diode. Suitable LEDs may be those having a nominal wavelength ranging, for example, from about 340 nm to about 520 nm, such as 340 nm, or 385 nm, or 470 nm, or 500 nm. In one example, the blue or UV light source 50 emits light wavelengths ranging from about 300 nm to about 520 nm at various intensities.

One or more light sources 50 may be used to release NO from the NO donor/adduct. The use of multiple light sources 50 may enable further control over the NO release. For example, if higher levels of NO are desirable, all of the light sources 50 facing the container 32 (or coating/film of the NO donating formulation) may be activated to emit light toward the NO donor/adduct, and if lower levels of NO are desirable, less than all of the light sources 50 may be activated. In some examples, the NO generating formulation 10, 10' is designed to release a prescribed volume of NO gas when it is exposed to light wavelengths ranging from about 300 nm to about 520 nm at various intensities.

In some examples, the system 47 further includes control electronics 52 operatively connected to the blue or UV light source 50, and a battery 24 operatively connected to the control electronics 52. The battery 24 may be a coin battery or other suitable power source for the light source 50 and control electronics 52.

Some examples of the system 47 further include an NO sensor 38, a nitrogen dioxide ($NO_2$) sensor, or combinations thereof.

The example shown in FIG. 24A includes the NO sensor 38 positioned in the housing 48; and the control electronics 52 positioned in the housing 48. Electronic circuitry (e.g., control electronics 52) may be operatively connected to the light source 50 to control when the source(s) 50 is/are turned ON and OFF, the duration of an ON cycle, the intensity, the power surface density, etc. In one example, the control electronics 52 control the power of the light source 50 in order to generate a predetermined volume of NO gas.

The control electronics 52 may also be part of a sensing and feedback system, which includes the NO sensor 38 and the feedback controller 40 (not shown in FIG. 24A). The sensing and feedback system may also include an $NO_2$ sensor (not shown in FIG. 24A). The feedback from the NO sensor 38 and the $NO_2$ sensor may be used to servo-regulate one or more parameters of the light source(s) 50 to achieve an at least substantially constant concentration of NO at the delivery end.

While the light activated NO generating system 47 in FIG. 24A is shown attached within a face mask 12, it is to be understood that the light activated NO generating system in FIG. 24A may be incorporated into other inhalation devices. In one example, the light activated NO generating system 47 shown in FIG. 24A is separate from, and in fluid communication with, the inhalation device. In these examples, the light activated NO generating system 47 shown in FIG. 24A may further include a tube including a first end that is fluidly connected to the housing 48, and an adapter at a second end of the tube that is distal to the first end, the adapter to attach to an inhalation device, such as a face mask 12, a nasal cannula 34, or a breathing tube (or ventilator). In this example, the NO gas molecules are generated within the housing 48 upon exposure to blue and/or UV light, and then the NO gas molecules are transported through the tube to the inhalation device, which they are delivered to a user/patient. These examples may also include a fan or suction device to transport the NO from the housing 47 to the adapter. In one specific example, the inhalation device shown in FIG. 8 may be modified to include the light activated NO generating system 47. In this particular example, the container 34 and the air humidifier 22 shown in FIG. 8 may be replaced with the light activated NO generating system 47 shown in FIG. 24A.

While the tube and adapter have been described with the light activated NO generating system 47, it is to be understood that these components may be used in a similar manner with any of the moisture activated systems disclosed herein. In some of these examples, an air humidifier 22, an air pump 20 and a source of electrical power would be included in order to introduce the effective amount of water vapor to a housing that contains the container 32 and the NO generating formulation 10, 10' therein.

Figure 24B:
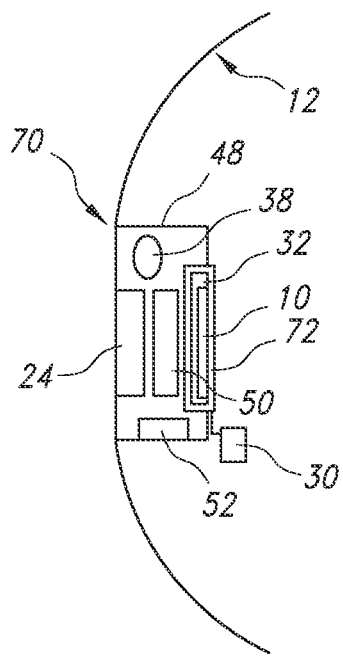
FIG. 24B is a schematic illustration of another example of a light activated NO generating system affixed to an inhalation device.

When the NO donor/adduct is light and moisture activatable, it is to be understood that humidity and/or hydrating liquid and/or UV or blue light 50 may be used to activate the NO donor/adduct in the NO generating formulation 10. An example of this hybrid system 70 is shown in FIG. 24B. In this example, the light activated NO generating system 47 (of FIG. 24A) may include an additional chamber 72 surrounding the container 32 (containing the NO generating formulation 10, 10', which is formed of the first solid formulation). This chamber 72 is liquid impermeable so that any introduced liquid or moisture does not interfere with the components of the light activated NO generating system 47. This chamber 72 includes one wall (facing the light source(s) 50) that is transparent to the emitted UV or blue light, and another wall (facing the interior of the inhalation device) that is NO permeable. The chamber 72 may receive a hydrating liquid that can activate the NO donor/adduct or may be operatively connected to an air humidifier 22 that can introduce moisture sufficient to activate the NO donor/adduct.

Figure 25C:
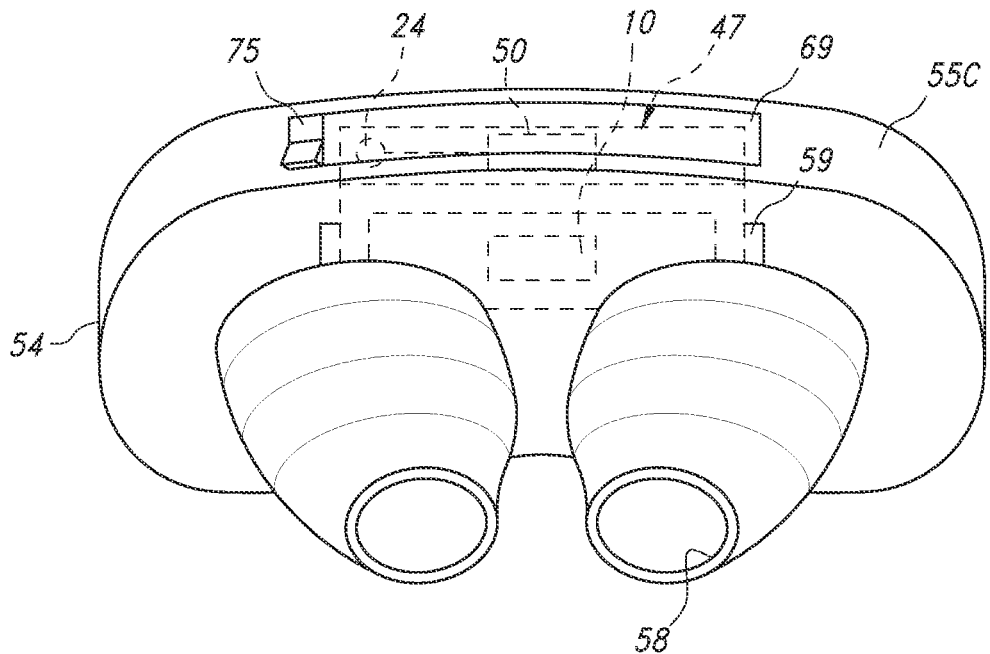
FIG. 25C is a perspective and schematic illustration of a nose vent plug including a light activated NO generating system therein.

Still other examples of the NO generating systems are shown in FIG. 25A, FIG. 25B, and FIG. 25C. These example systems include nose vent plugs or nose pillows. Each of the nose vent plugs includes a nitric oxide (NO) impermeable housing 54 having integrally formed walls 55A, 55B, 55C that define a partially enclosed interior portion 57; two nasal protrusions 58 extending from one of the integrally formed walls 55A and in fluid communication with the partially enclosed interior portion 57; and an air vent 56 defined in another of the integrally formed walls 55C to introduce air flow into the partially enclosed interior portion 57; and a receptacle 59 in the partially enclosed interior portion 57, the receptacle 59 containing an NO generating formulation or to receive an NO generating formulation.

The nitric oxide (NO) impermeable housing 54 may be formed of any NO impermeable material. The material used to manufacture the housing 54 should not include silicone or other materials that are known to interact with (e.g., absorb) NO.

The integrally formed walls 55A, 55B, 55C and the nasal protrusions 58 of the housing 54 may be one continuous piece of material that is molded, 3D printed, etc.

The nose vent plug housing 54 includes an introduction vent or vents 56. The vent(s) 56 may be strategically placed so that air is drawn over the NO generating formulation and into one of the nasal protrusions 58. It may be desirable for the vent(s) 56 to be placed at or near the sides of the housing 54 (in wall 55C) as opposed to the top of the housing 54. This placement may prevent the NO from escaping through the vent(s) 56. This placement may also help to create headspace in the enclosed interior portion 57 where the NO concentration can build during exhalation and during the period of rest time in the user's natural breathing cycle. The stored NO is then available as a pulsed concentration during inhalation (described further below).

Each vent 56 may also be operatively associated with a fin (not shown) that is positioned to help guide the air to flow into the enclosed interior portion 57 (toward the NO generating formulation) through the vent 56.

The nasal protrusions 58 may be shaped so that they are insertable into a user's nostrils, or they may be shaped so that they can be placed outside of, but within proximity of, the user's nostrils. For example, the nasal protrusions 58 may fit snugly just below the user's nostrils. In the latter example, the housing 54 may include a head strap 74 (shown in FIG. 25B) to hold the nasal protrusions 58 in the desired position on the user's face. As such, some examples of the NO generating system further includes a head strap 74 secured to the housing 54. The housing 54 may include additional holes or another attachment mechanism (e.g., hook and loop fasteners) to secure the head strap 74. The head strap 74 may also be adjustable. It is to be understood that the nasal protrusions 58 may be flush with the wall 55A (and thus not true protrusions), and the head strap 74 may be used to hold the nose plug vent adjacent to the user's nostrils.

The nose vent plug further includes a receptacle 59 within the enclosed interior portion 57. Different examples of the receptacle 59 are shown in FIGS. 25A-25C. The receptacle 59 hold the NO generating formulation (in liquid form, or in any of the solid forms disclosed herein, etc.) in effective proximity to the air vent(s) 56 and the nasal protrusions 58.

Referring specifically to FIG. 25A, the receptacle 59 is to receive the container 32 having the first or second solid formulations (e.g., the NO generating formulation 10, 10') therein. In an example, the first or second solid formulation may be included as a single solid or a plurality of the single solids in the container 32. The container(s) 32 may be positioned between the introduction vent 56 and the inhalation openings 58. This positioning enables moisture and/or air from the vent(s) 56 and, in some instances, from the user's exhaled breath to enter the container 32 and to activate the first or second solid formulation contained therein. This positioning also enables generated NO gas molecules to be inhaled by the user through the nasal penetrations 58.

During use, the user breathes in and out through the nasal penetrations 58. The moisture in the inhaled air may be sufficient to activate the first or second solid formulation (e.g., NO generating formulation 10, 10'). In other examples, the nose vent plug housing 54 may also include an air humidifier 22 secured to the housing 54, and that generates moisture. As shown in FIG. 25A, the system may also include a fan (e.g., air pump 20) secured to the housing 54. The fan can push the moisture (from the vent(s) 56 or the air humidifier 20) toward the first or second solid formulation.

In the example shown in FIG. 25A, the NO generating formulation 10, 10' includes the stable NO donor/adduct (i.e., the first solid formulation) or the nitrite source (i.e., the second solid formulation) that is activatable when exposed to an effective amount of water vapor; the NO generating formulation 10, 10' is contained within the NO permeable container 32; and the receptacle 59 includes one of a wall to affix the NO permeable container 32; or slot to hold the NO permeable container 32. A receptacle wall may protrude into the center of the housing 54 and may receive, for example, the adhesive 42 (similar to the example shown in FIG. 22) or snap to a clip 46 (similar to the example shown in FIG. 23). The receptacle slots (shown in FIG. 25A) can fix the container 32 into place.

In one example, the container 32 is permanently affixed by the receptacle 59, and in another example, the container 32 is removably affixed by the receptacle 59. When the container 32 (and thus the first or second solid formulation) are permanently fixed within the housing 54 (e.g., through the adhesive 42 or the slots), the entire nose vent plug may be disposable (e.g., after its useful life is spent). When the container 32 (and thus the NO generating formulation 10, 10') is removably fixed within the housing 54 (e.g., through the slots), the nose vent plug is reusable. In these examples, a new container 32 (and new first or second solid formulation) may be introduced into the housing 54 and secured by the receptacle 59.

When the nose vent plug is reusable, the housing 54 may further include a door 69 defined in one of the integrally formed walls 55C (at the top of the nose vent plug), wherein the door 69 being movable between a closed position and an open position that provides access to the receptacle 59. An example of the door 69 is shown in FIG. 25B.

Referring now specifically to FIG. 25B, some examples of the receptacle 59 include a reservoir 60 to receive a liquid form 73 of the NO generating formulation.

In one of these examples, the system may include a solid form of the NO generating formulation 10, 10' (e.g., the first solid formulation or the second solid formulation disclosed herein) that is re-constitutable in a hydrating liquid to generate the liquid form 73 prior to the liquid form 73 being introduced into the reservoir 60. The hydrating liquid may be added to the solid form to generate the liquid form 73, which is then introduced into the reservoir 60 through the door 69.

Other examples of the receptacle 59 include the reservoir 60, but further include an absorbent pad 71 (e.g., cotton, pressed cotton, etc.) that is one of: contained in the reservoir 60 and to be wet with the liquid form of the NO generating formulation (e.g., reconstituted first solid formulation or second solid formulation); or to be wet with the liquid form of the NO generating formulation and then introduced into the reservoir 60. In some examples, the absorbent pad 71 is incorporated into the reservoir 60, and any example of the liquid form 73 is then incorporated into the reservoir 60. In other examples, the absorbent pad 71 is wet with any example of the liquid form 73 outside of the nose vent plug, and then is the incorporated into the reservoir 60. In still other examples, the absorbent pad 71 contains a solid form of the NO generating formulation (e.g., the first or second solid formulation) that is re-constitutable in the hydrating liquid. In this example, the solid form of the NO generating formulation includes an S-nitrosothiol (RSNO) powder or nitroprusside, or a nitrite source. For example, the absorbent pad 71 may include a coating of the solid/powder form of the NO generating formulation, and this coated absorbent pad 71 is incorporated into the reservoir 60. In some examples, the solid or powder is poured onto the absorbent pad 71 or placed into the reservoir 60 prior to the absorbent pad 71 (and thus is under the absorbent pad 71).

The hydrating liquid (depending on the NO generating chemistry in the coating) is then introduced into the reservoir 60 to activate the NO donor/adduct or the nitrite source.

In any of these examples, the absorbent pad 71 can stabilize the liquid form 73 of the NO generating formulation.

The receptacle 59 that is a reservoir 60 may include walls that are impermeable to the hydrating liquid and that are NO permeable.

The receptacle 59/reservoir 60 may be sized so that a head space is created in the enclosed interior portion 57. In the head space, the outgassed NO can concentrate (e.g., during the user's pause in breathing and the time it takes to breath out) through an exhalation check valve (i.e., an air divert valve) that diverts air flow around the enclosed interior portion 57, thereby allowing a higher concentration of NO to gather in the head space. The stored NO is then available as a pulsed concentration during inhalation (described further below).

Referring now specifically to FIG. 25C, some examples of the receptacle 59 can receive a cartridge, such as the light activated NO generating system 47, 70 as described in FIG. 24A or 24B. In this example, the NO generating formulation is blue or UV light activatable; and the NO generating system further comprises a cartridge (e.g., system 47 or 70) inserted in, or to be inserted in the receptacle 59, the cartridge containing the NO generating formulation; a blue or UV light source 50 positioned to illuminate the NO generating formulation; and a battery 24 operatively connected to the blue or UV light source 50. The cartridge operates the same as the system 47 shown and described in FIG. 24A or the system 70 shown and described in FIG. 24B. In short, the activated blue or UV light source illuminates the NO generating formulation to generate NO molecules that are delivered to the user through the nasal protrusions 58.

The example shown in FIG. 25C can further include an NO sensor 38 positioned in the cartridge and control electronics 52 positioned in the cartridge. This example can include an on/off switch 75 located on the exterior of the housing 54 that turns the blue or UV light source 50 on or off. This example of the nose vent plug may be disposable or reusable.

Any example of the nose vent plug (including those shown in FIGS. 25A, 26B, and 25C) may also include an air divert valve (exhalation check valve 16') to channel exhaled air out of the housing 54. This valve can keep the exhaled breath away from the NO generating formulation so that NO introduction to the user is maximized. The air divert valve may be controlled by control electronics 52 (e.g., an electronic controller) that are connected to a sensor feedback loop and an NO sensor 38. The data from the sensor 38 can be used to divert air out of the housing 54 or allow it to remain in the housing 54 so that a user receives a suitable level of NO. The valve can also be controlled to a closed position so that NO in the headspace in the enclosed interior portion 57 can build during exhalation and during the period of rest time in the user's natural breathing cycle. The control electronics 52 could operate a fan or other mechanism to force a pulsed concentration during the user's inhalation.

Any example of the inhalation device disclosed herein may also include a nitrogen dioxide ($NO_2$) filter. The $NO_2$ filter may be positioned, e.g., in a tube of a nasal cannula or ventilator, or within a face mask, or in the nasal protrusions 58 of a nose vent plug, to receive the output gas NO before it is inhaled by the patient. Any example of the $NO_2$ filter described herein may be used. As examples, any of the nose vent plugs shown in FIGS. 25A-25C may further comprises the filter positioned between the receptacle 59 and the nasal protrusions 58, where the filter including an absorbent to scavenge nitrogen dioxide ($NO_2$) released by the NO generating formulation, a reagent to convert generated $NO_2$ back to NO, or combinations thereof.

Moreover, in any of the examples disclosed herein that utilize any of the liquid forms of the NO generating formulation, an additional NO permeable membrane may be positioned on the reservoir 60. In some instances, aerosol droplets may be generated as well as the NO gas. Aerosol droplets are undesirable for various medical applications. It is to be understood that the NO permeable membrane prevents any aerosol droplets from being generated and/or from leaving the reservoir 60 with the NO gas. Examples of the type of NO permeable membrane that prevent aerosol droplets from forming include porous polytetrafluoroethylene (PTFE), polypropylene, polyethylene, polyamide, polyvinylidene difluoride, etc. An example of the type of NO permeable membrane that prevents aerosol droplets from leaving includes polycarbonate, such as polycarbonate track etch membranes.

Other mechanisms for prevent aerosol droplets from being transported with the NO gas stream include positioning a highly porous droplet catcher (e.g., gauze).

In any of these examples, this type of NO permeable membrane may be positioned at an opening of the reservoir 60, or specifically in the nose vent plug, between the opening of the reservoir 60 and the nasal protrusions 58, or in the nasal protrusions 58.

The examples disclosed herein can generate effective amounts of NO for delivery to a user/patient via inhalation. The increased levels of NO that are generated may be therapeutic, and may be sufficient to help kill bacteria and viruses, disrupt bacterial biofilm formation, disperse or prevent microbial biofilm formation (e.g., disperse antibiotic resistant biofilms), reduce platelet aggregation and thrombosis, reduce inflammation, and increase ciliary beat frequency, thus improving mucociliary clearance. Elevated NO production with examples of the present disclosure may be observed nearly immediately and for an extended period (e.g., up to about 4-96 hours).

In some of the examples disclosed herein, the levels of gas-phase NO within the sinus cavities/airways as a result of inhaling gaseous nitric oxide generated from the moisture activated NO generating formulation may range between about 50 parts-per-billion-volume (ppbv) and about 7500 ppbv levels. In other of the examples disclosed herein, the NO generating formulation contained in a pouch or other container 32 releases a desired volume of NO, such as an average of 10 ppm, 20 ppm, or 30 ppm with a design range of 1 ppm to 250 ppm for a range of time from 0.5 to 3 hours or more, if desirable. In the example of the nose pillow (nose vent plug), the NO generating capacity of any example of the re-constituted NO generating formulation (e.g., liquid form 73) can be made in the range of 5 ppm to 50 ppm with a design range of 1 ppm to 250 ppm as may be desirable.

To further illustrate the present disclosure, examples are given herein. It is to be understood that these examples are provided for illustrative purposes and are not to be construed as limiting the scope of the present disclosure.

It is to be understood that the NO release data discussed below and regarding FIG. 9 et seq. was generated from pellets without a plastic sheath thereon.

EXAMPLES

Example 1

Formulations

The moisture activated NO releasing formulations were all prepared in a similar manner. The components were mixed together thoroughly until the mixture appeared homogeneous. The mixture was then placed into a circular hand pill press, such as one with a 5 mm diameter. The mixture was compressed to form a solid pellet. The pellet was then removed by additionally pressing the pellet after removal of the bottom stop. This produced a pellet around 10 mm long and 5 mm in diameter, the size of which can be varied depending on the target gas generating capacity of the design.

NO Release Rate

The NO release rate of the formulations was measured by an electrochemical nitric oxide analyzer (NOA) at room temperature in an amber NOA cell, while purging with 50 mL/min humidified nitrogen (about 80% relative humidity (RH)) through a glass pipette.

Stability Measurements

The stability of the formulations was tested via UV/Vis analysis and/or via the electrochemical NOA.

GSNO Results

FIGS. 9-20 depict the NO release kinetics of the various formulations tested.

Figure 9:
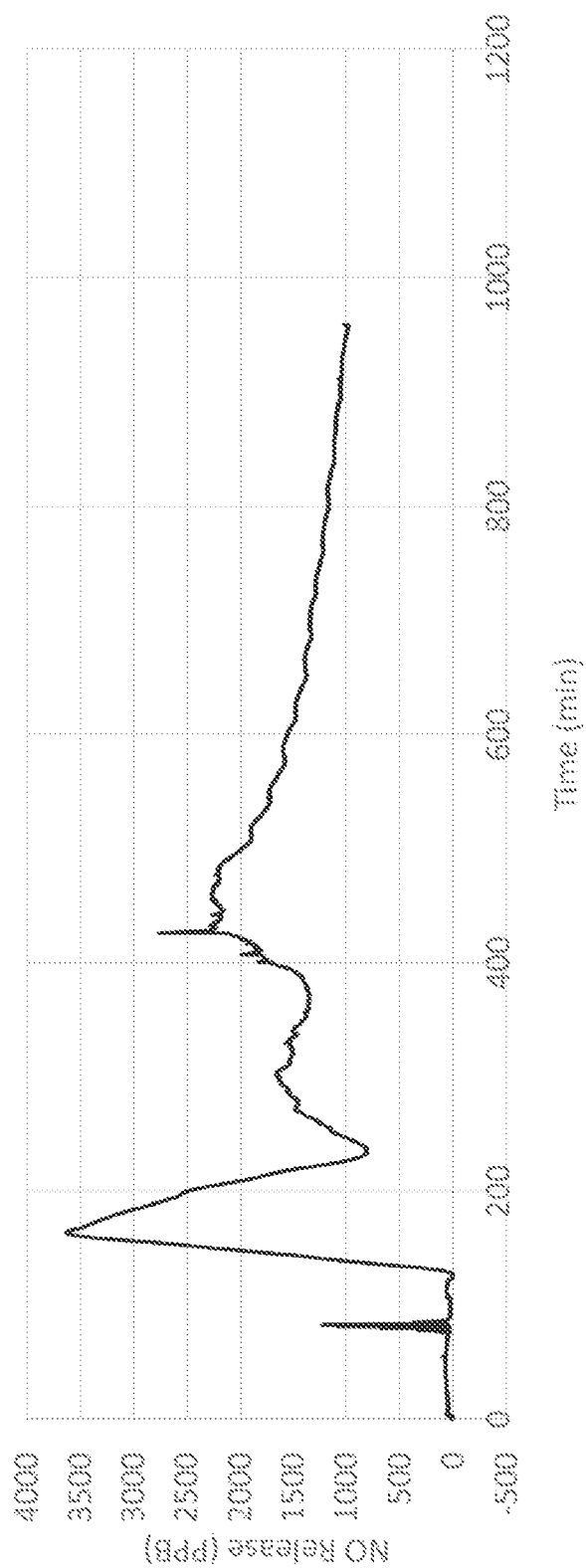
FIG. 9 is a graph depicting the nitric oxide (NO) release profile from an example of the NO generating formulation with respect to time.

Formulation A, FIG. 9, used GSNO, ascorbic acid (3.5 wt %) as the accelerant, and corn starch as the hydrophilic binder (71 wt %), along with an inert salt (a mixture of sodium chloride and sodium bicarbonate) (21.5 wt %). The pellets of this mixture crumbled easily.

Figure 10:
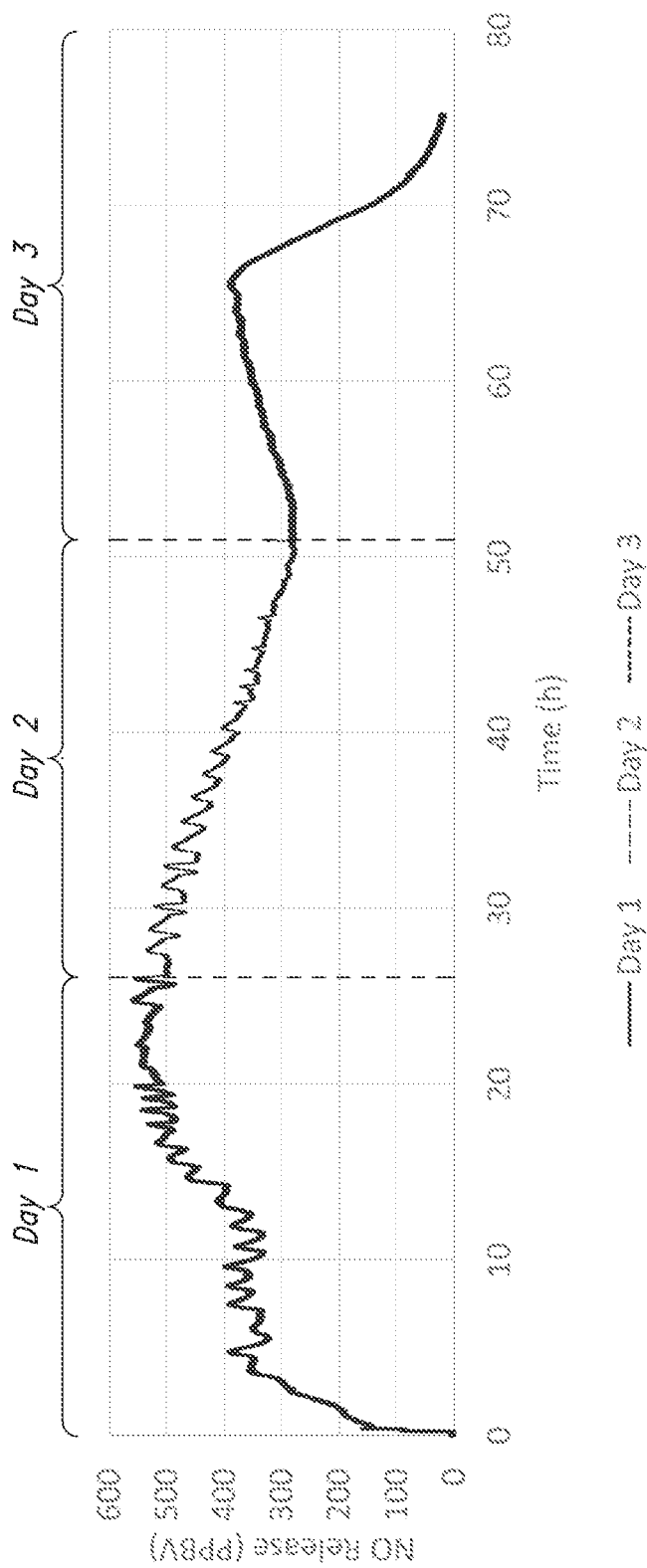
FIG. 10 is a graph depicting the nitric oxide (NO) release kinetics of GSNO from another example of the NO generating formulation.

Formulation B, FIG. 10, used GSNO (6.4 wt %), ascorbic acid (13.8 wt %) as the accelerant, and used, for the hydrophilic binder (79.8 wt %), a commercial excipient mixture (FIRMAPRESS™ excipient) that is representative of common mixtures used to make pills for ingestion. This improved the cohesion of the pill.

Figure 11:
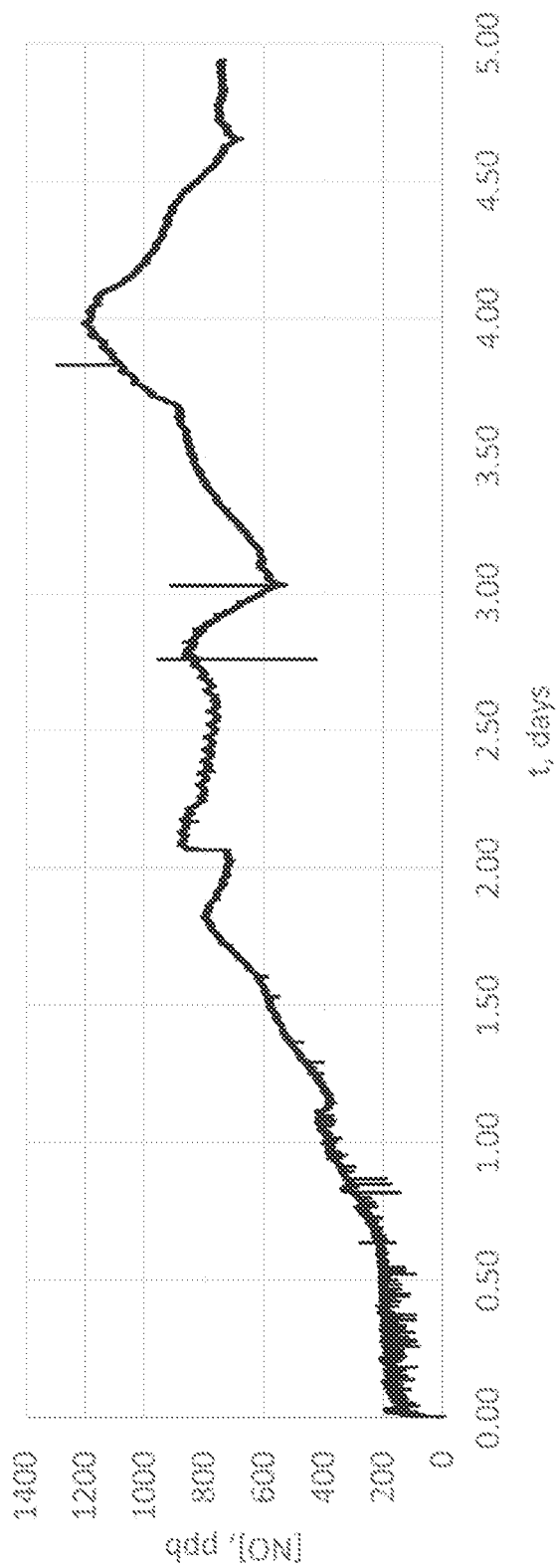
FIG. 11 is a graph depicting the nitric oxide (NO) release profile from yet another example of the NO generating formulation with respect to time.

Formulation C, FIG. 11, used GSNO (10.6 wt %), ascorbic acid (22.9 wt %) as the accelerant, and hypromellose as the hydrophilic binder (71 wt %). Hypromellose is another common ingredient in making ingestible pills for a commercial excipient formulation. This formulation was not as mechanically robust as the prior formulation B.

Figure 12:
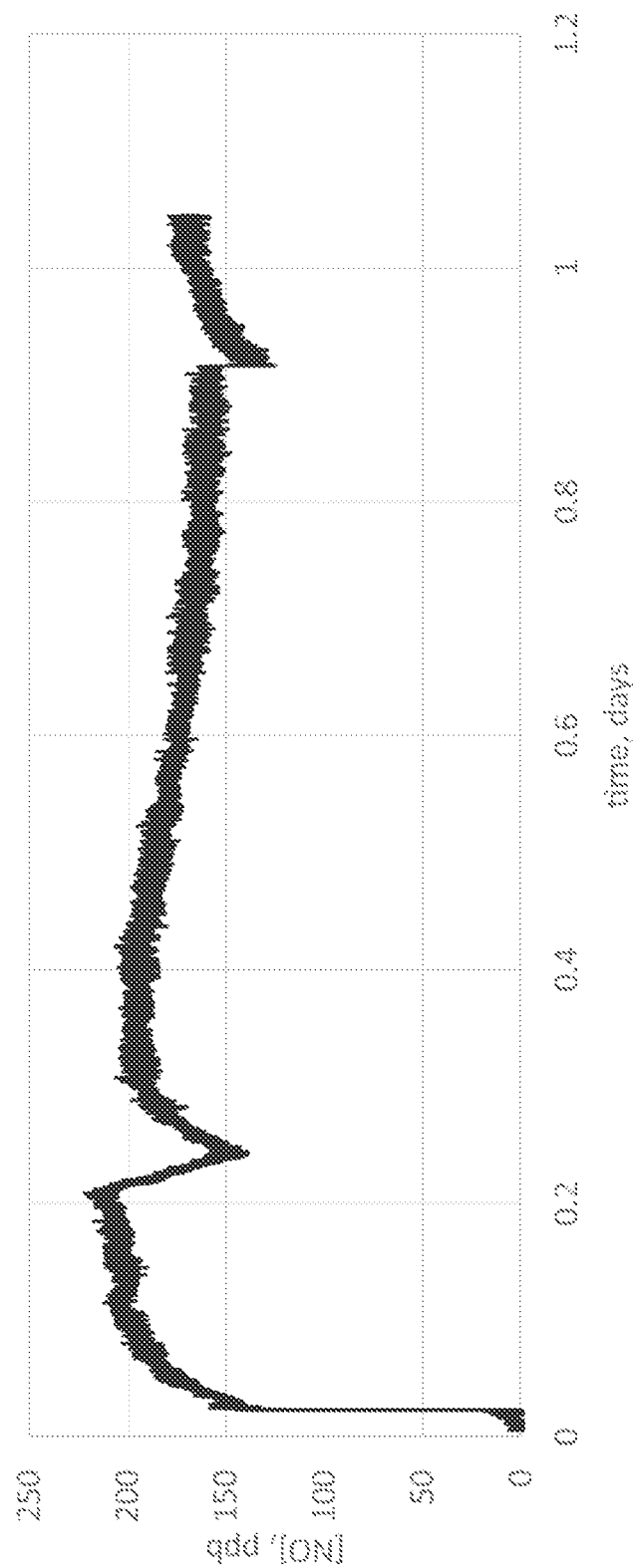
FIG. 12 is a graph depicting the nitric oxide (NO) release profile from still another example of the NO generating formulation with respect to time.

Formulation D, FIG. 12, used GSNO (8.1 wt %), ascorbyl palmitate (41.1 wt %) as the accelerant, with the palmitate acting as a lubricant, and hypromellose as the hydrophilic binder (50.8 wt %). As compared to formulation C, this improved the pill pressing properties since it lubricates the press. This also shows that the addition of lubricant lowers the rate of NO release.

Figure 13:
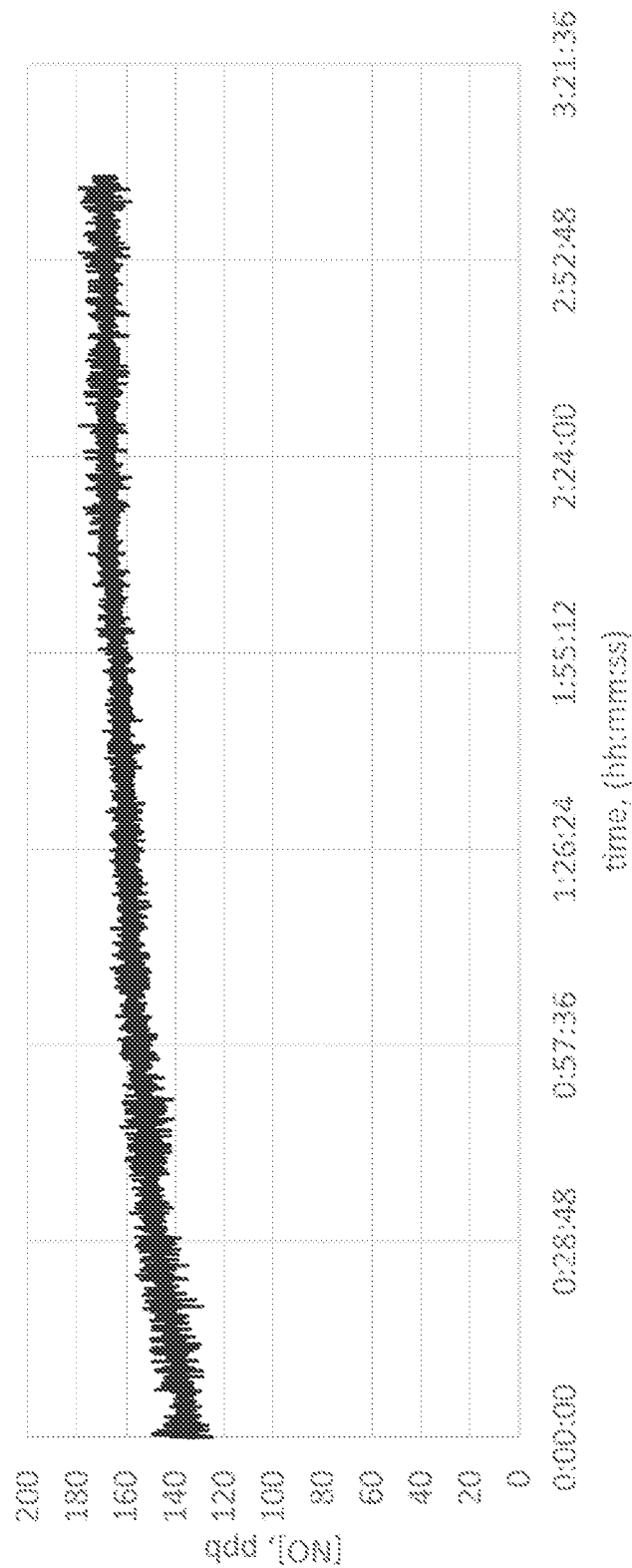
FIG. 13 is a graph depicting the nitric oxide (NO) release profile from the example of the NO generating formulation of FIG. 12 with respect to time.

FIG. 13 shows another batch of formulation D. This shows that the NO release kinetics are similar between batches.

Figure 14:
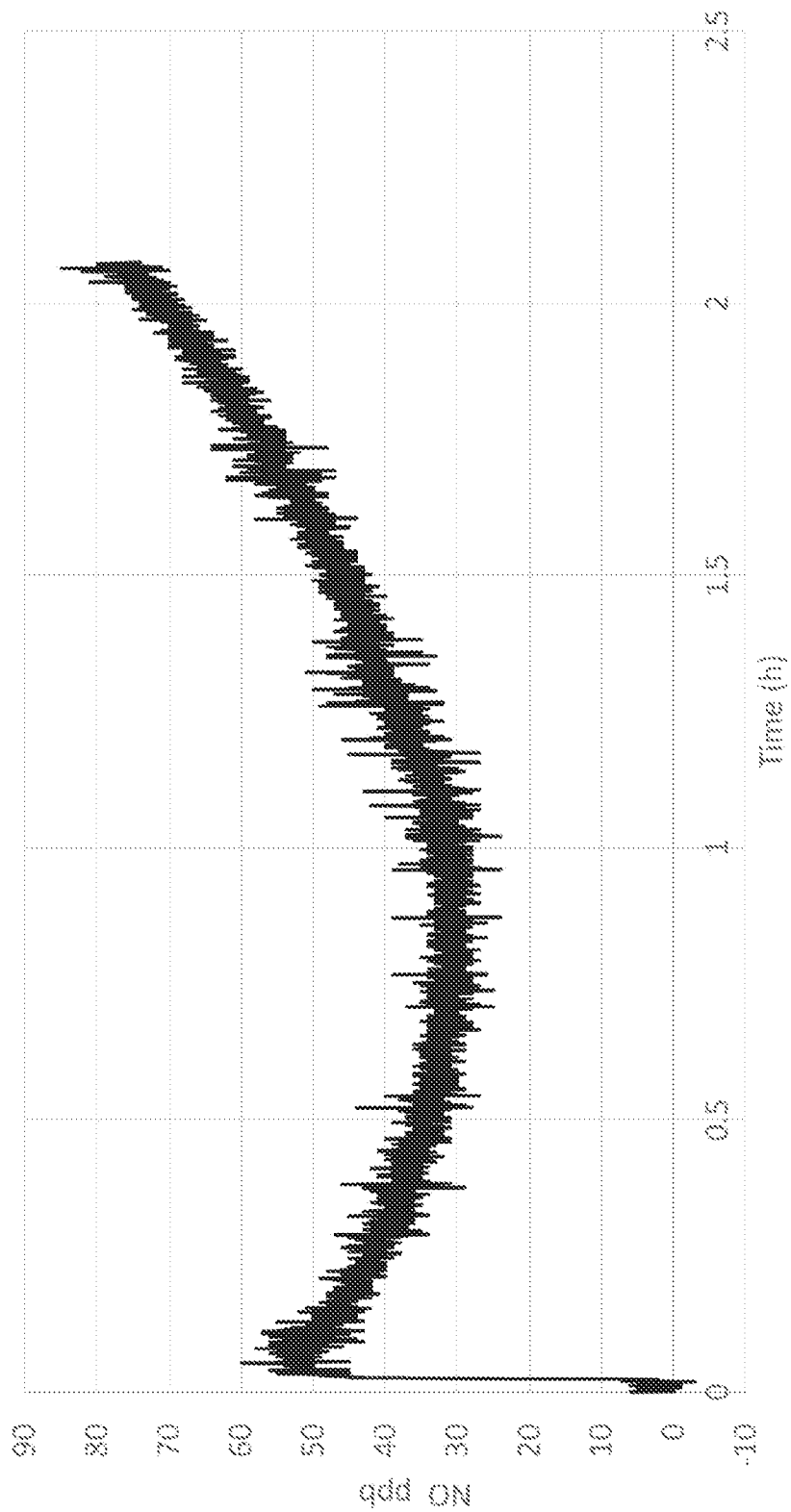
FIG. 14 is a graph depicting the nitric oxide (NO) release profile from a further example of the NO generating formulation with respect to time.

Formulation E, FIG. 14, which included only 1% GSNO in the formulation, along with ascorbic acid (about 10 wt %) as the accelerant and about 90% hydrophilic binder, produced around 50 ppbv of NO.

Figure 15A:
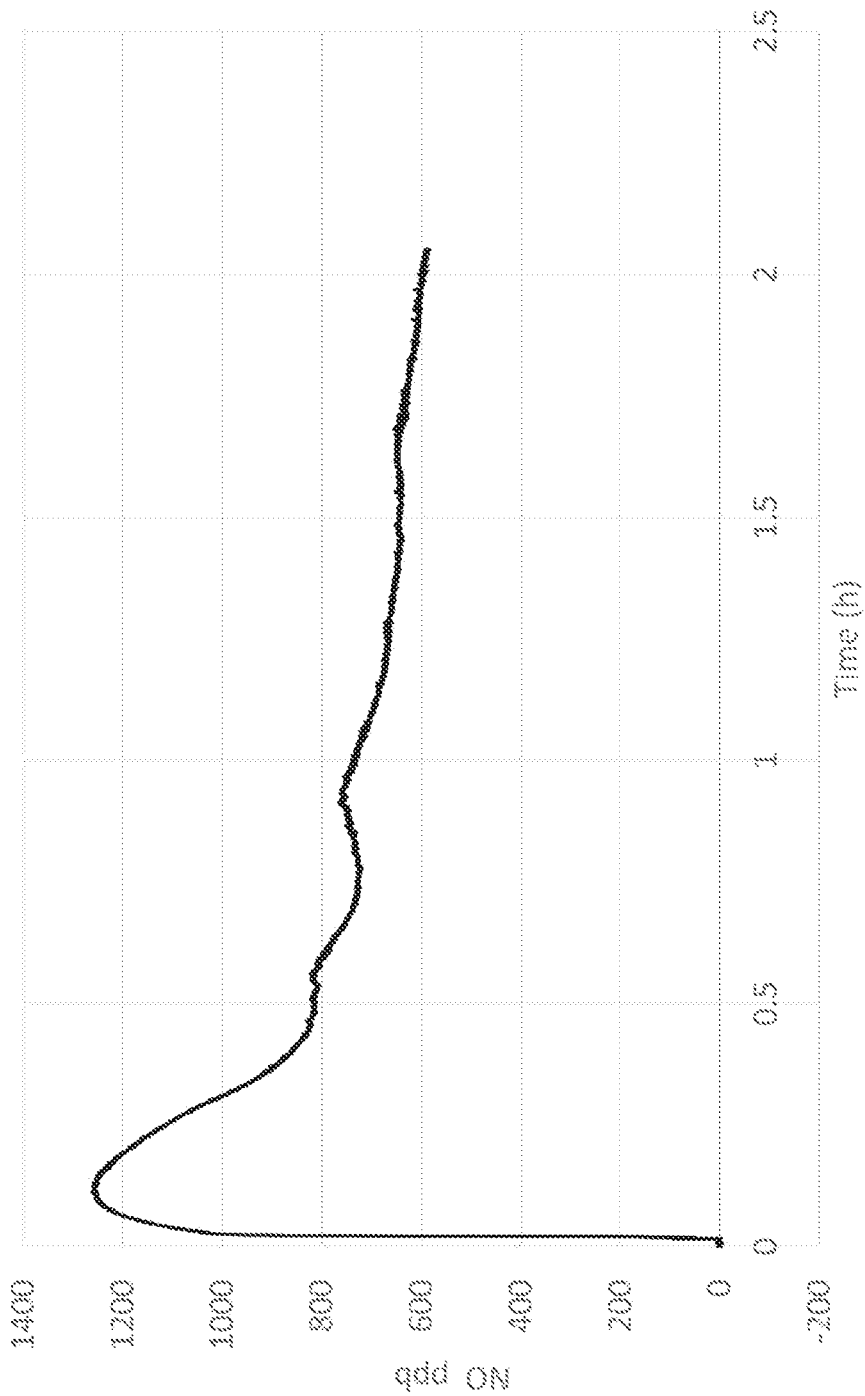
FIG. 15A is a graph depicting the nitric oxide (NO) release profile from a further example of the NO generating formulation with respect to time.

Formulation F included GSNO (40 wt %), cysteine (25 wt %) as the accelerant, and hypromellose as the hydrophilic binder (35 wt %). The NO release with Formulation F (high percentage of GSNO and cysteine) is shown in FIG. 15A.

Figure 15B:
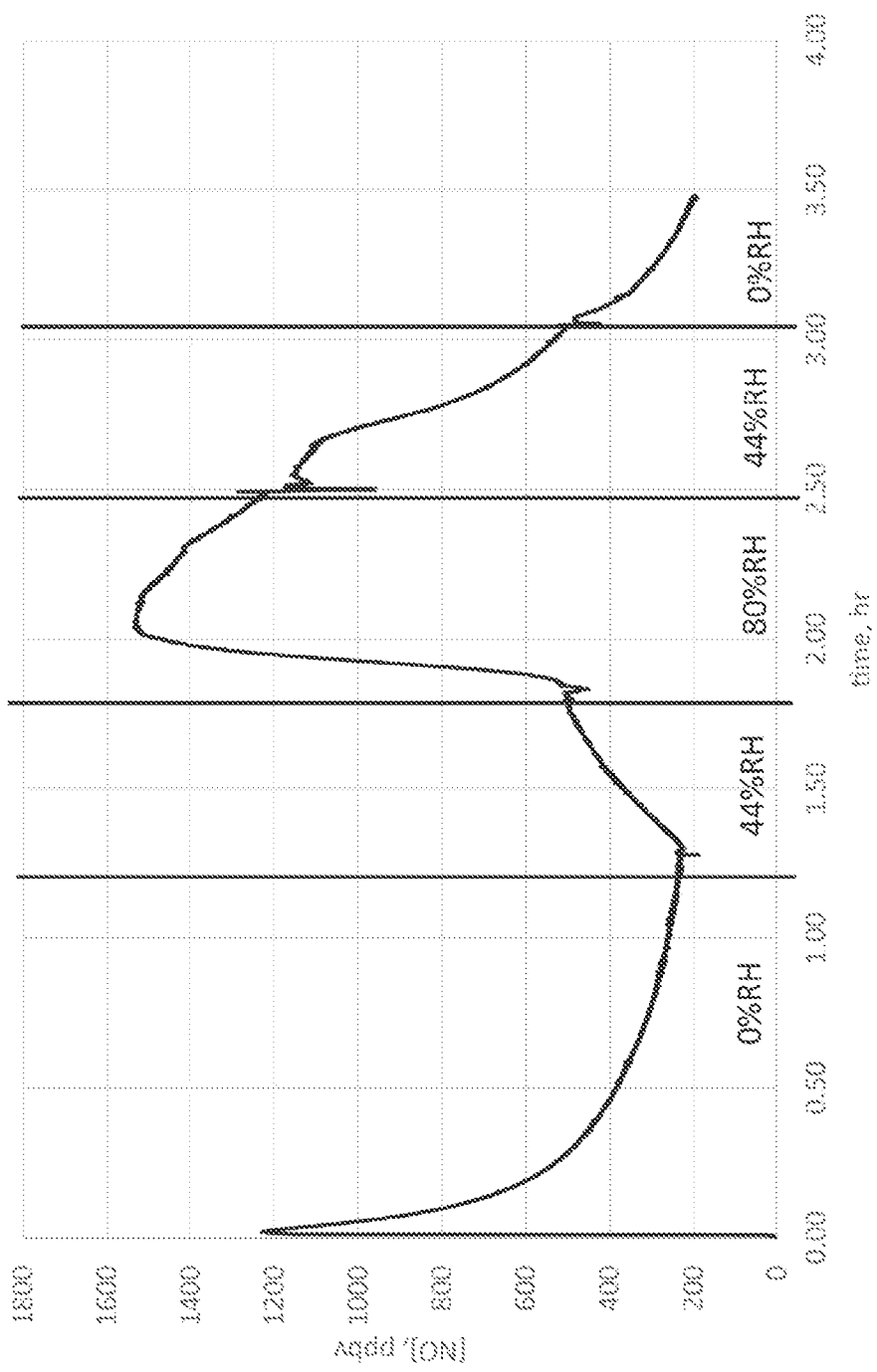
FIG. 15B is a graph depicting the nitric oxide (NO) release kinetics of GSNO the example formulation of FIG. 15A, at various relative humidity conditions.

Formulation F, FIG. 15B shows the dependence of NO generation on percent relative humidity (% RH). At zero humidity the rate of NO generation is relatively low, less than 200 ppbv and even this may likely be due to small amounts of residual moisture in the system. At moderate humidity, about 44% RH, the rate is substantially higher, and at very high humidity, about 80% RH, the rate is 3 times that at 44% RH.

Figure 16:
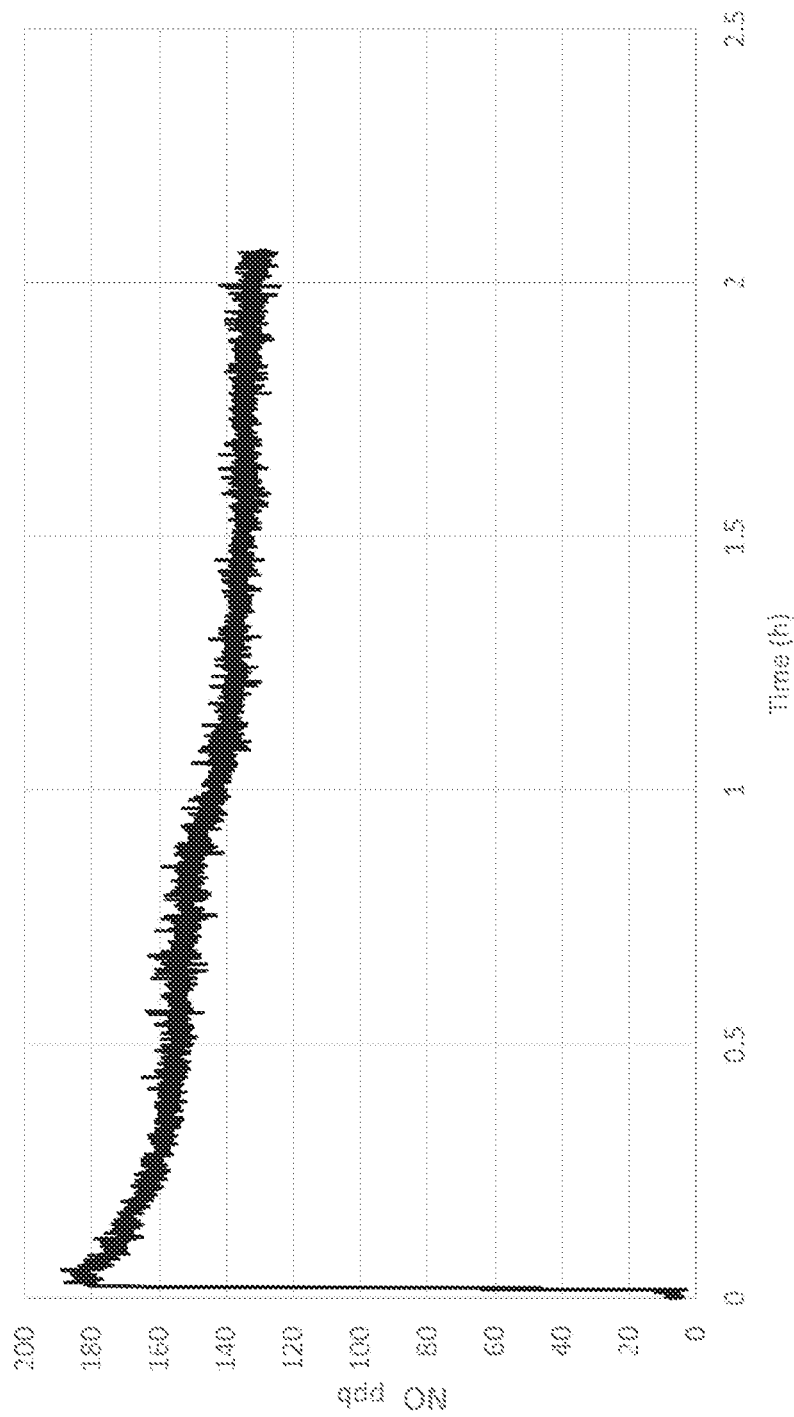
FIG. 16 is a graph depicting the nitric oxide (NO) release profile from a further example of the NO generating formulation with respect to time.

Formulation G, FIG. 16, shows that a very high percentage of accelerant, 60% ascorbyl palmitate, can generate effective NO levels. Formulation G also included 12 wt % GSNO and 25 wt % of the FIRMAPRESS™ excipient as the hydrophilic binder.

Figure 17:
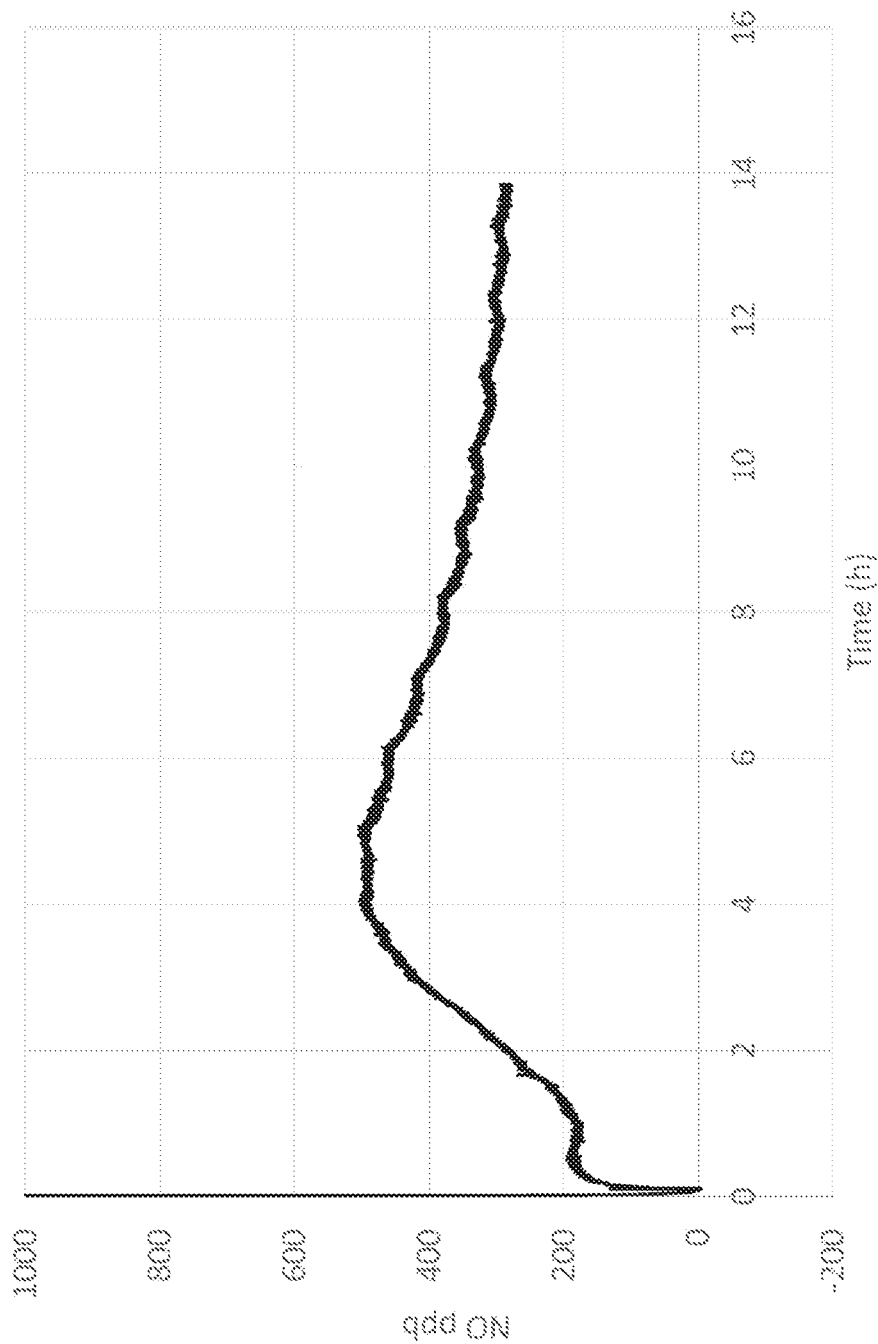
FIG. 17 is a graph depicting the nitric oxide (NO) release profile from a further example of the NO generating formulation with respect to time.

Formulation H, FIG. 17, shows that a very low percentage of accelerant, 0.8% copper sulfate, can generate effective NO levels. Formulation H also included 8 wt % GSNO and 91 wt % of hypromellose as the hydrophilic binder.

Figure 18:
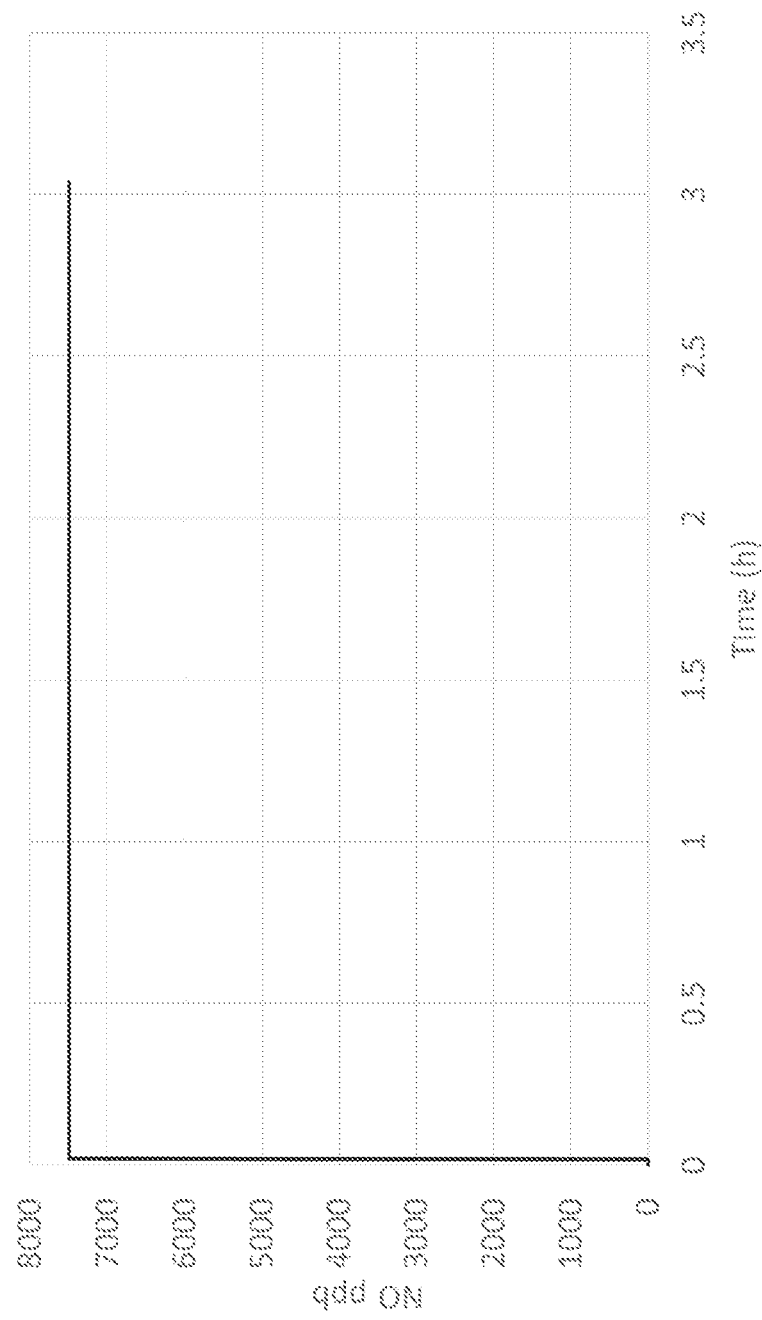
FIG. 18 is a graph depicting the nitric oxide (NO) release profile from a further example of the NO generating formulation with respect to time.

Formulation I, FIG. 18, shows that a hydrophilic compound, calcium chloride (a deliquescent salt) (62 wt %), in conjunction with glutathione (30 wt %) as the accelerant is very effective at causing NO generation. Formulation I also included 8 wt % of GSNO.

Figure 19:
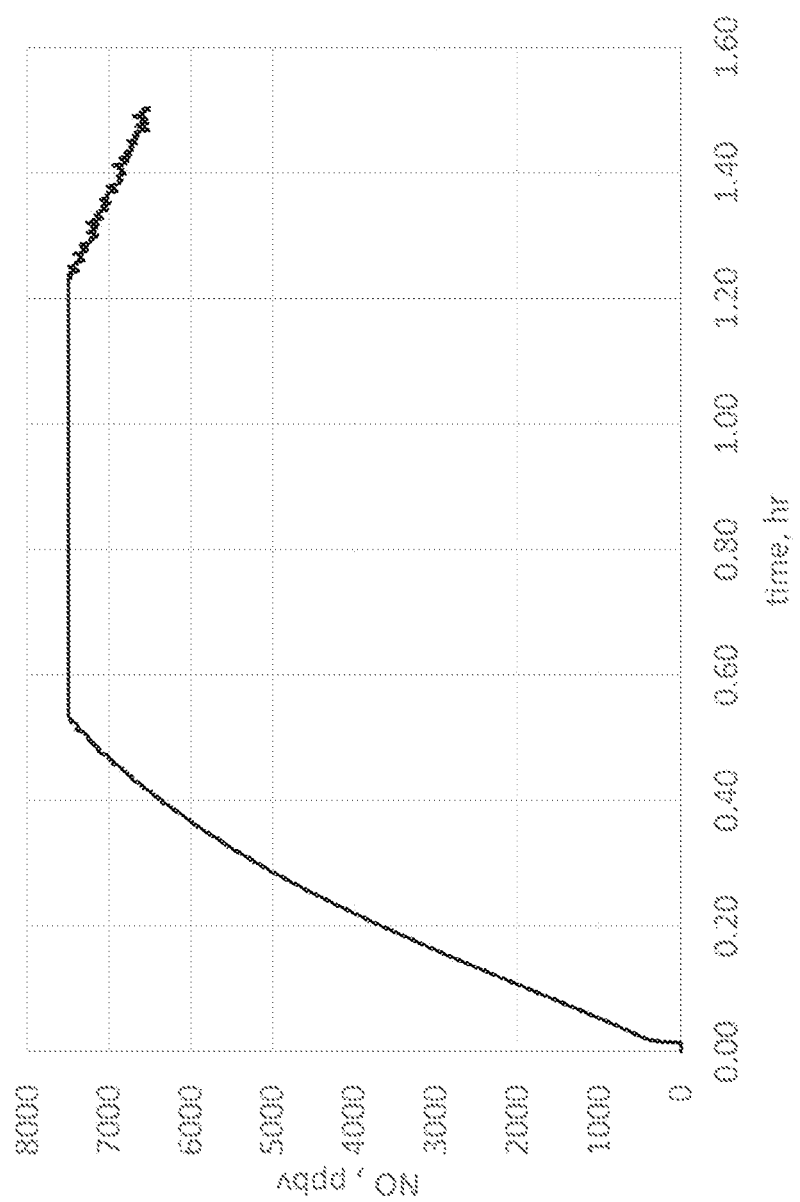
FIG. 19 is a graph depicting the nitric oxide (NO) release profile from a further example of the NO generating formulation with respect to time.

Formulation J, FIG. 19, shows NO generation with a high level of a salt, disodium hydrogen phosphate (46 wt %). Formulation J also included 7 wt % of GSNO, 15 wt % of ascorbic acid as the accelerant, and 32 wt % of a hypromellose (24 wt %) and FIRMAPRESS™ excipient (8 wt %) mixture as the hydrophilic binder.

Figure 20:
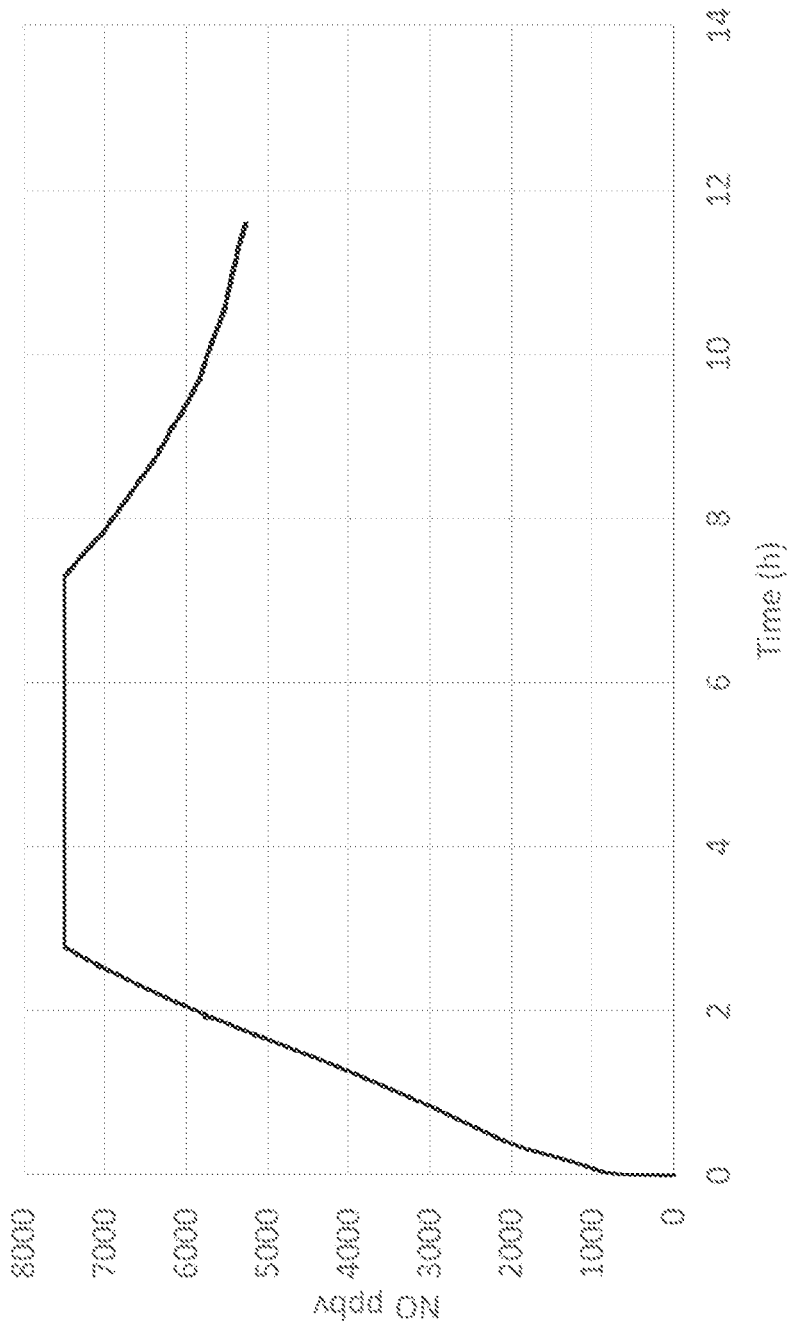
FIG. 20 is a graph depicting the nitric oxide (NO) release profile from a further example of the NO generating formulation with respect to time.

Formulation K included 8 wt % GSNO, 50 wt % disodium hydrogen phosphate, and 42 wt % of the FIRMAPRESS™ excipient. Formulation K, FIG. 20, shows that a base, disodium hydrogen phosphate (50 wt %), that produces an alkaline pH when dissolved is effective as an accelerant (RSNOs are relatively unstable in alkaline conditions).

GSNO instability and hence NO generation begins to increase above pH 8.5. The instability increases as the pH increases above 8.5.

Example 2

A nose vent plug (or nose pillow) similar to that shown in FIG. 25B was prepared.

An NO donor formulation was prepared that included sodium nitrite, sodium ascorbate, sodium dihydrogen phosphate, and disodium hydrogen phosphate. 1.5 mL of deionized (DI) water was also added. Table 1 illustrates the components of the NO donor formulation.

TABLE 1

NO Donor Formulation

| Component | Wt (g) | Wt % | mmol | M |
|---|---|---|---|---|
| Sodium nitrite | 0.23 | 30.4 | 3.3333 | 2.222 |
| Sodium Ascorbate | 0.3 | 39.7 | 1.7034 | 1.136 |
| Sodium Dihydrogen Phosphate | 0.1 | 13.2 | 0.8333 | 0.556 |
| Disodium Hydrogen Phosphate | 0.126 | 16.7 | 0.8873 | 0.592 |
| Total | 0.756 | | | |

Figure 27:
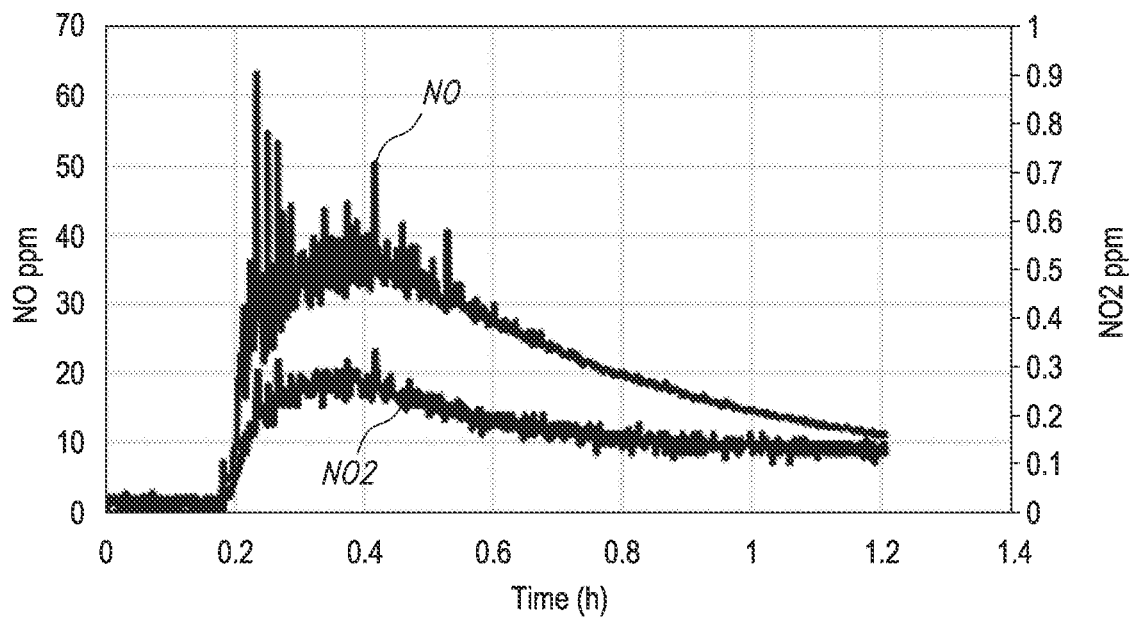
FIG. 27 is a graph depicting the NO levels (ppm, left Y axis) and $NO_2$ levels (ppm, right Y axis) versus time (hours, X axis).

The NO donor formulation was introduced into the reservoir of the nose vent plug. A steady air flow was directed through the vents at a flow rate of 7.5 L/min. The NO and $NO_2$ levels were measured at the nasal protrusions. The results are shown in FIG. 27. These results indicate that NO is generated in desirable levels. $NO_2$ levels may be further decreased by incorporating an oxygen scrubber and/or a filter.

Throughout this disclosure, a variety of chemicals have been described. It is to be understood that some of these chemicals may have synonyms (depending upon the nomenclature convention) and/or abbreviations (depending upon the vendor) that are not set forth herein, but are intended to be encompassed by the disclosure.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from about 3 wt % to about 12 wt % should be interpreted to include not only the explicitly recited limits of about 3 wt % to about 12 wt %, but also to include individual values, such as 5 wt %, 6.2 wt %, 9.85 wt %, etc., and sub-ranges, such as from about 4 wt % to about 10 wt %, etc. Furthermore, when "about" is utilized to describe a value, this is meant to encompass minor variations (up to +/−10%) from the stated value.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:

1. A moisture or hydrating liquid activatable solid formulation for nitric oxide (NO) generation, comprising:
   a nitrite source that is to generate NO when exposed to an effective amount of moisture or a hydrating liquid, the nitrite source being selected from the group consisting of ammonium nitrites, alkyl nitrites, dicyclohexylamine nitrite, phosphazine nitrites, and nitrite salts;
   a copper (I) or copper (II) catalyst;
   an NO generation accelerant present in an amount of from about 27 wt % to about 50 wt % based on a total weight of the moisture or hydrating liquid activatable solid formulation; and
   a pH buffer present in a total amount of from about 1 wt % to about 32 wt % based on the total weight of the moisture or hydrating liquid activatable solid formulation, the pH buffer being a monobasic or a dibasic phosphate,
   wherein a pH of the moisture or hydrating liquid activatable solid formulation is from greater than 4 to about 9.0.

2. The moisture or hydrating liquid activatable solid formulation as defined in claim 1 wherein the copper (I) or copper (II) catalyst is selected from the group consisting of copper salts, copper oxides, copper hydroxides, copper hydrates, copper sulfides, copper selenides, copper pyrophosphates, copper phosphates, copper selenites, copper carboxylates, copper acetonitriles, copper acrylates, copper thiolates, copper dithiolates, organo-copper compounds, copper alkyl-oxides, copper phosphines, solid phase copper complexes, copper ligand complexes, and combinations thereof.

3. The moisture or hydrating liquid activatable solid formulation as defined in claim 1 wherein the NO generation accelerant is a reducing agent of the nitrite source or an additional catalyst.

4. The moisture or hydrating liquid activatable solid formulation as defined in claim 1 wherein:
   the nitrite source is present in an amount ranging from about 1 wt % to about 80 wt % based on a total weight of the moisture or hydrating liquid activatable solid formulation; and
   the copper (I) or copper (II) catalyst is present in an amount ranging from about 0.1 wt % to about 50 wt % based on the total weight of the moisture or hydrating liquid activatable solid formulation.

5. The moisture or hydrating liquid activatable solid formulation as defined in claim 1, further comprising an oxygen scrubber present in an amount ranging from about 0.1 wt % to about 20 wt % based on the total weight of the moisture or hydrating liquid activatable solid formulation.

6. The moisture or hydrating liquid activatable solid formulation as defined in claim 1, further comprising a hydrophilic binder present in an amount ranging from about 0.1 wt % to about 90 wt % based on the total weight of the moisture or hydrating liquid activatable solid formulation.

7. The moisture or hydrating liquid activatable solid formulation as defined in claim 1, further comprising a lubricant present in an amount ranging from about 0.1 wt % to about 90 wt % based on the total weight of the moisture or hydrating liquid activatable solid formulation.

8. The moisture or hydrating liquid activatable solid formulation as defined in claim 1, further comprising a hydration agent present in an amount ranging from about 0.1 wt % to about 50 wt % based on the total weight of the moisture or hydrating liquid activatable solid formulation.

9. The moisture or hydrating liquid activatable solid formulation as defined in claim 1, further comprising an $NO_2$ scavenger present in an amount ranging from about 1 wt % to about 30 wt % based on the total weight of the moisture or hydrating liquid activatable solid formulation.

10. The moisture or hydrating liquid activatable solid formulation as defined in claim 1, further comprising a desiccant present in an amount ranging from about 0.1 wt % to about 30 wt % based on the total weight of the moisture or hydrating liquid activatable solid formulation.

11. An NO generating system, comprising:
    a face mask;
    a housing secured to an interior of the face mask, the housing including a reservoir with an NO permeable wall positioned between the housing an interior of the face mask; and
    a moisture or hydrating liquid activatable solid formulation for NO generation to be introduced into the reservoir, the moisture or hydrating liquid activatable solid formulation including:
        a nitrite source that is to generate NO when exposed to an effective amount of moisture or a hydrating liquid, the nitrite source being selected from the group consisting of ammonium nitrites, alkyl nitrites, dicyclohexylamine nitrite, phosphazine nitrites, and nitrite salts;
        a copper (I) or copper (II) catalyst;
        an NO generation accelerant present in an amount of from about 27 wt % to about 50 wt % based on a total weight of the moisture or hydrating liquid activatable solid formulation; and
        a pH buffer present in a total amount of from about 1 wt % to about 32 wt % based on the total weight of the moisture or hydrating liquid activatable solid formulation, the pH buffer being a monobasic or a dibasic phosphate,
        wherein a pH of the moisture or hydrating liquid activatable solid formulation is from greater than 4 to about 9.0.

12. The NO generating system as defined in claim 11 wherein the moisture or hydrating liquid activatable solid formulation further includes a hydrophilic binder, a lubricant, a hydration agent, an oxygen scrubber, an $NO_2$ scavenger, a desiccant, and combinations thereof.

13. The moisture or hydrating liquid activatable solid formulation as defined in claim 1 wherein the nitrite source is the nitrite salt, and wherein the nitrite salt is present in an amount of from about 1 wt % to about 25 wt % based on the total weight of the moisture or hydrating liquid activatable solid formulation.

14. The moisture or hydrating liquid activatable solid formulation as defined in claim 13 wherein the nitrite salt is selected from the group consisting of sodium nitrite and potassium nitrite.

15. The moisture or hydrating liquid activatable solid formulation as defined in claim 1 wherein:
    the formulation includes the copper (II) catalyst;
    the copper (II) catalyst is present in an amount of from about 5 wt % to about 7 wt % based on the total weight of the moisture or hydrating liquid activatable solid formulation;
    the nitrite source is the nitrite salt;
    the nitrite salt is selected from the group consisting of sodium nitrite and potassium nitrite;

the nitrite salt is present in an amount of from about 10 wt % to about 25 wt % based on the total weight of the moisture or hydrating liquid activatable solid formulation;

the NO generation accelerant is an ascorbate; and the pH buffer is present in an amount of from about 16 wt % to about 28 wt % based on the total weight of the moisture or hydrating liquid activatable solid formulation.

16. The moisture or hydrating liquid activatable solid formulation as defined in claim 1, further comprising a lubricant selected from the group consisting of sodium stearate, magnesium stearate, and ascorbyl palmitate, and wherein the lubricant is present in an amount of from about 1 wt % to about 13 wt % based on the total weight of the moisture or hydrating liquid activatable solid formulation.

17. The moisture or hydrating liquid activatable solid formulation as defined in claim 1 wherein the moisture or hydrating liquid activatable solid formulation is free of an S-nitrosothiol (RSNO).

18. The moisture or hydrating liquid activatable solid formulation as defined in claim 1 wherein the formulation is free of a desiccant.

* * * * *